(12) United States Patent
Takimiya

(10) Patent No.: US 8,816,100 B2
(45) Date of Patent: Aug. 26, 2014

(54) COMPOUND, METHOD OF PRODUCING THE COMPOUND, ORGANIC SEMICONDUCTOR MATERIAL AND ORGANIC SEMICONDUCTOR DEVICE

(71) Applicant: Hiroshima University, Hiroshima (JP)

(72) Inventor: Kazuo Takimiya, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days.

(21) Appl. No.: 14/062,545

(22) Filed: Oct. 24, 2013

(65) Prior Publication Data

US 2014/0051865 A1 Feb. 20, 2014

Related U.S. Application Data

(62) Division of application No. 13/130,551, filed as application No. PCT/JP2009/068660 on Oct. 30, 2009.

(30) Foreign Application Priority Data

Nov. 21, 2008 (JP) ................................ 2008-298830
Mar. 27, 2009 (JP) ................................ 2009-080527

(51) Int. Cl.
*C07D 495/04* (2006.01)

(52) U.S. Cl.
CPC .................. *C07D 495/04* (2013.01)
USPC ......................................................... 549/42

(58) Field of Classification Search
USPC ......................................................... 549/42
See application file for complete search history.

(56) References Cited

U.S. PATENT DOCUMENTS

| 5,110,829 A | 5/1992 | Kober et al. |
| 5,936,259 A | 8/1999 | Katz et al. |
| 2009/0001357 A1 | 1/2009 | Takimiya et al. |
| 2009/0065770 A1 | 3/2009 | Miura et al. |

FOREIGN PATENT DOCUMENTS

| JP | H11-195790 | 7/1999 |
| JP | 2005-206750 | 8/2005 |
| JP | 2007-67262 | 3/2007 |
| JP | 2007-269775 | 10/2007 |
| JP | 2008-147256 | 6/2008 |
| JP | 2008-258592 | 10/2008 |
| JP | 2009-267134 | 11/2009 |
| WO | WO2006/077888 | 7/2006 |
| WO | WO2007/105386 | 9/2007 |

OTHER PUBLICATIONS

Collin, J. , "Resistance A L'Impact Electronique Et Aux Radiations De Quelques Composes Organiques A Caractere Aromatique", Bulletin Des Societes Chimiques Belges, vol. 72, Jan. 1963, pp. 38-49.
Coropceanu, et al., "Vibronic Coupling inOrganic Semiconductors: The Case of Fused Polycyclic Benzene-Thiophene Structures", Chemistry a European Journal, Jan. 10, 2006, pp. 2073-2080.
Desai, et al., "Thiophenes and thiapyrans. XXV. Condensed thiophenes and thiapyrans from 1,5-,1,4-, and 1,3-dimercaptonaphthalenes", Journal of Scientific & Industrial Research, vol. 20B, 22-30, p. 20B, 22-30, Columbus, Ohio, USA: Chemical Abstracts, vol. 55, 1961, pp. 23486-23488.
King, F et al., "Bioisosteres, Conformational Restriction, and Pro-Drugs—Case History: An Example of a Conformational Restriction Approach", Chapter 14: Med. Chem: Principle & Practice., 1994, pp. 206-208.
Sunthankar, et al., "A New Synthesis of Thiophenes and Thiapyrans", Proc. of the India Academy of Sciences, Section A, vol. 32, issue 6, Dec. 1950, pp. 396-401.
Tilak, B.D. , "Synthesis of thiophenes and thiapyrans. IV. Thiophenes and thiapyrans from naphthalenethiols", Proceedings—Indian Academy of Sciences, Section A, vol. 33A, 71-7, pp. 33A, 71-7, Columbus, Ohio, USA: Chemical Abstracts, vol. 46, 1951, pp. 4525b-4525g.
Umeda, et al., "Formation of naphthodithiophene isomers by flash vacuum pyrolysis of 1,6-di(2-thienyl)- and 1,6-di(3thienyl)-1,5-hexadien-3-ynes", Science Direct, Comptes Rendus Chimie, vol. 12, No. 3-4, Nov. 28, 2008, pp. 378-384.

*Primary Examiner* — Taofiq A Solola
(74) *Attorney, Agent, or Firm* — Michael A. Glenn; Perkins Coie LLP

(57) ABSTRACT

There are provided a novel compound having a good field mobility, a method of producing of the compound, an organic semiconductor material containing the novel compound, and an organic semiconductor device. The novel compound which is represented by the following general formula (1), (2), (3) or (4) (where Z represents a sulfur atom or a selenium atom, and R represents a hydrogen atom, an alkyl group or a phenyl group in general formulae) has a structure having two benzene rings of naphthalene bonded with a thiophene ring and a selenophene ring, respectively. These compounds have a conjugate system in molecules due to an interaction between π orbitals, and show a strong molecular interaction through a sulfur atom or a selenium atom contained in a thiophene ring or a selenophene ring in each molecule, thereby having a good field mobility.

11 Claims, 5 Drawing Sheets

COMPOUND, METHOD OF PRODUCING THE COMPOUND, ORGANIC SEMICONDUCTOR MATERIAL AND ORGANIC SEMICONDUCTOR DEVICE

CROSS REFERENCES TO RELATED APPLICATIONS

This application is a divisional of U.S. application Ser. No. 13/130,551, filed May 20, 2011, which is a U.S. National Phase application of International Patent Application No. PCT/JP2009/068660 filed 30 Oct. 2009, and claims priority to Japanese Patent Application No. 2008-298830 filed on 21 Nov. 2008 and Japanese Patent Application No. 2009-080527 filed 27 Mar. 2009. The disclosures of the above Patent Applications are incorporated herein by reference in its entirety.

TECHNICAL FIELD

The present invention relates to a novel compound, a method of producing the compound, an organic semiconductor material and an organic semiconductor device.

BACKGROUND ART

Recently, thin-film devices using organic semiconductor materials, such as organic EL (Electro Luminescence) devices, organic FET (Field Effect Transistor) devices, and organic thin-film photoelectric conversion devices, are getting attention, and become in a practical use.

The mobility of electronic charge carrier (hereinafter, simply referred to as a carrier) is important in the basic physicality of the organic semiconductor materials used for such thin-film devices. For example, in the case of an organic EL device, the mobility of carrier affects the transportation efficiency of charge. The transportation efficiency of charge is important for improvement of the luminescent efficiency and for the low-voltage driving. Moreover, in the case of an organic FET device, the mobility of carrier directly affects the switching speed of a transistor and the performance of a device to be driven. Hence, the mobility of carrier is also important for the practical use of an organic FET device and the improvement of the performance.

Under such a circumstance, various organic compounds available as the organic semiconductor materials are researched and exploited. Compounds having a benzene-thiophene skeleton are studied as compounds having an appropriate carrier mobility. Non-patent Literature 1 exemplifies compounds having various benzene-thiophene skeletons.

PRIOR ART DOCUMENT

Non-patent Literature

Non-patent Literature 1: Vibronic Coupling in Organic Semiconductors: The Case of Fused Polycyclic Benzene-Thiophene Structures; Veaceslav Coropceanu, Ohyun Kwon, Brigitte Wex, Bilal R. Kaafarani, Nadine E. Gruhn, Jason C. Durivage, Douglas C. Neckers and Jean-Luc Bredas; Chem. Eur. J. 2006, Vol. 12, p. 2073-2080

DISCLOSURE OF INVENTION

Problem to be Solved by the Invention

Non-patent Literature 1 discloses a structural formula of compounds having a naphthalene-thiophene skeleton. Such compounds are, however, not successfully synthesized so far, i.e., non-existent compounds. According to the conventional knowledge for organic synthetic chemistry, it is extremely difficult to introduce a thiophene ring into a naphthalene skeleton.

It is an object of the present invention to provide a novel compound which has a naphthalene-thiophene skeleton or a naphthalene-selenophene skeleton and has a good carrier mobility, a method of producing the compound, and an organic semiconductor material and an organic semiconductor device including such a compound.

Means for Solving the Problem

A compound according to a first aspect of the present invention is represented by a following general formula (1), (2), (3) or (4).

[Chemical Formula 1]

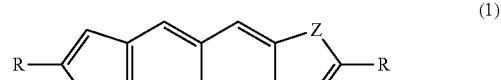

(1)

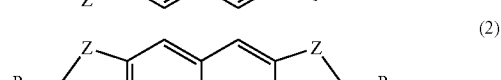

(2)

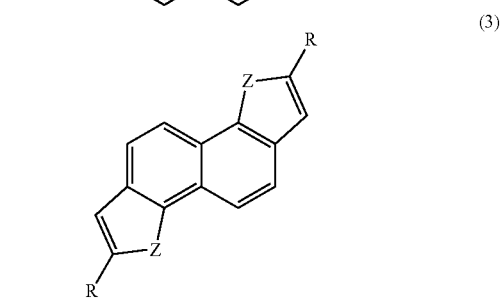

(3)

(4)

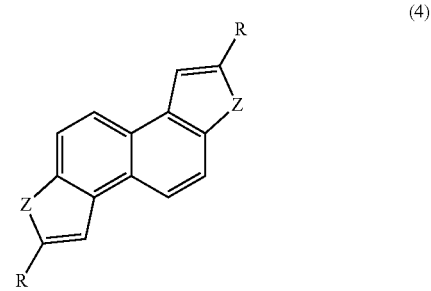

(where Z represents a sulfur atom or a selenium atom, and R represents a hydrogen atom, an alkyl group or a phenyl group in the above general formulae)

A compound according to a second aspect of the present invention is represented by a following general formula (5), (6), (7) or (8).

[Chemical Formula 2]

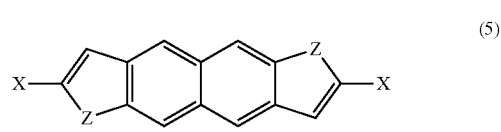

(5)

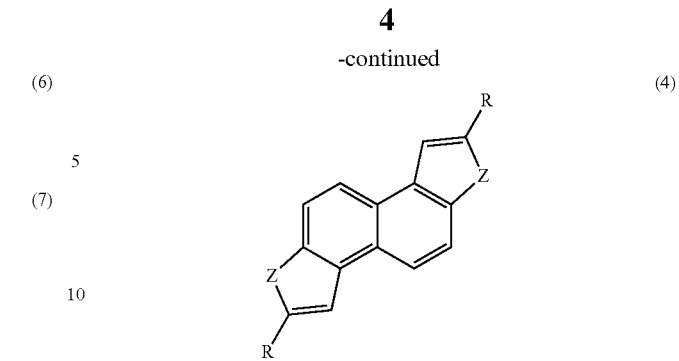

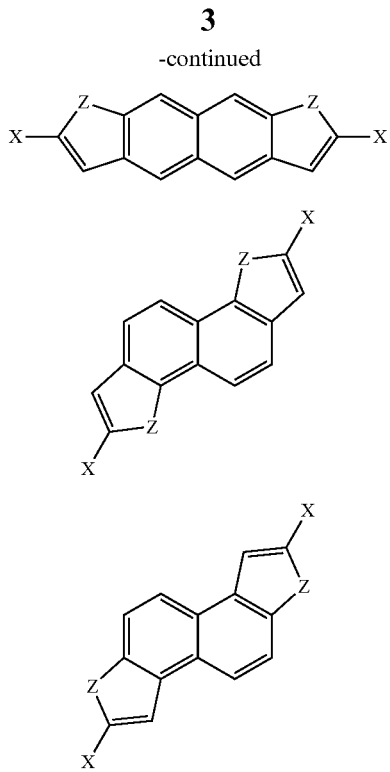

(where Z represents a sulfur atom or a selenium atom and X represents a halogen atom in the above general formulae)

According to a third aspect of the present invention, there is provided a method of producing a compound represented by a following general formula (1), (2), (3) or (4), the method comprising: a step of causing dihalogenodihydroxynaphthalene to react with an anhydrous trifluoromethanesulfonic acid in order to obtain dihalogeno-bis(trifluoromethanesulfonyl) naphthalene; a step of causing the dihalogeno-bis(trifluoromethanesulfonyl)naphthalene to react with a terminal acetylene compound in order to obtain a dihalogeno-diethynylnaphthalene derivative; and a step of causing the dihalogeno-diethynylnaphthalene derivative to react with sulfide salt or selenide salt.

[Chemical Formula 3]

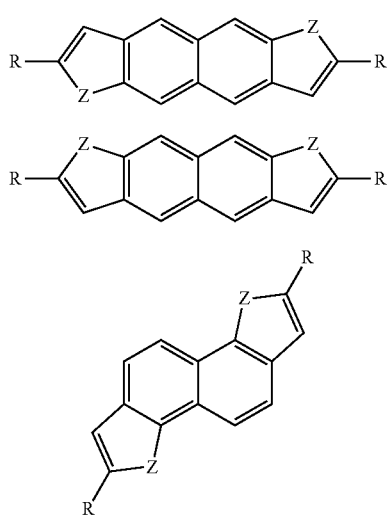

(where Z represents a sulfur atom or a selenium atom, and R represents a hydrogen atom, an alkyl group or a phenyl group in the above general formulae)

The compound production method of the third aspect of the present invention may further comprise a step of causing dihydroxynaphthalene to react with a halogenation agent in order to obtain the dihalogenodihydroxynaphthalene.

The dihydroxynaphthalene may be 2,6-dihydroxynaphthalene, and the compound obtained may be a compound represented by the general formula (1) or (3).

The dihydroxynaphthalene may be 2,7-dihydroxynaphthalene, and the compound obtained may be a compound represented by the general formula (2).

The dihydroxynaphthalene may be 1,5-dihydroxynaphthalene, and the compound obtained may be a compound represented by the general formula (4).

It is preferable that the halogenation agent should be a bromination agent or a chlorination agent.

It is preferable that the halogenation agent should be a bromination agent, the compound production method should further comprise a step of adding a catalyst that promotes bromination of the dihydroxynaphthalene, and the step of adding the bromination agent should be carried out equal to or greater than twice.

It is preferable that the terminal acetylene compound should be any one of the followings: trimethylsilylacetylene; phenylacetylene; and 1-decyne.

It is preferable that the reaction of the dihalogeno-bis(trifluoromethanesulfonyl)naphthalene with the terminal acetylene compound should be carried out in a polar solvent that can dissolve the dihalogeno-bis(trifluoromethanesulfonyl) naphthalene.

It is preferable that the polar solvent should be an aprotic polar solvent.

It is particularly preferable that the aprotic polar solvent should be dimethylformamide.

According to a fourth aspect of the present invention, there is provided a method of producing a compound represented by a following general formula (5), (6), (7) or (8),

[Chemical Formula 4]

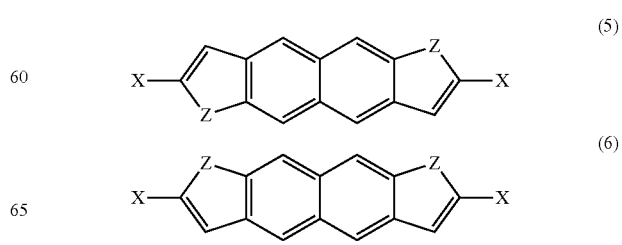

-continued (7)

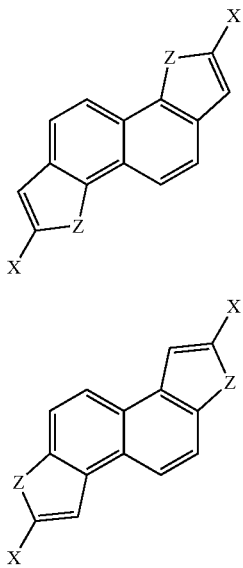

(8)

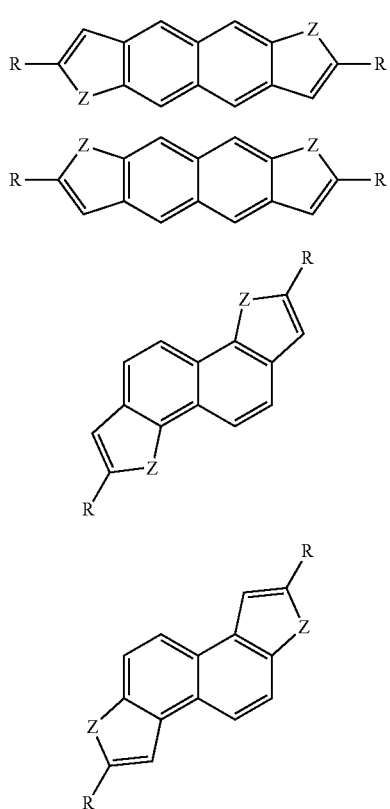

(where Z represents a sulfur atom or a selenium atom and X represents a halogen atom in the above general formulae)
the method comprising:
a step of adding a halogenation agent to a compound represented by a following general formula (1), (2), (3) or (4).

[Chemical Formula 5]

(1)

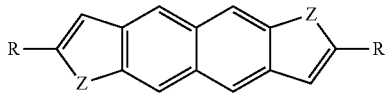

(2)

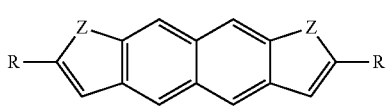

(3)

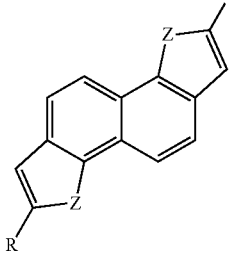

(4)

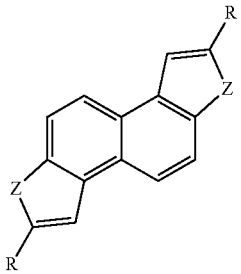

(where Z represents a sulfur atom or a selenium atom, and R represents a hydrogen atom in the above general formulae)

An organic semiconductor material according to a fifth aspect of the present invention contains at least one of following compounds represented by a following general formula (1), (2), (3) or (4).

[Chemical Formula 6]

(1)

(2)

(3)

(4)

(where Z represents a sulfur atom or a selenium atom, and R represents a hydrogen atom, an alkyl group or a phenyl group in the above general formulae)

An organic semiconductor device according to a sixth aspect of the present invention comprises the organic semiconductor material of the fifth aspect of the present invention.

Effect of the Invention

The compound of the present invention has a naphthalene-thiophene skeleton or a naphthalene-selenophene skeleton. The compound has a conjugate system in each molecule due to an interaction between π orbitals, and shows a strong molecular interaction through a sulfur atom or a selenium atom contained in a thiophene ring or a selenophene ring in each molecule. Hence, carriers can move efficiently. Because the compound of the present invention has good field mobility, such a compound can be used as an organic semiconductor material. This organic semiconductor material can be used for an organic semiconductor device.

Moreover, according to the production method of the compound of the present invention, it becomes possible to produce a compound having a naphthalene-thiophene skeleton or a naphthalene-selenophene skeleton through the form of a dihalogeno-diethynylnaphthalene derivative.

Furthermore, according to the production method of the compound of the present invention, it becomes possible to cause a hydrogen atom of naphthalene to be selectively subjected to halogenation. According to this method, the yield of the compound having a naphthalene-thiophene skeleton or a naphthalene-selenophene skeleton can be improved.

BEST MODE FOR CARRYING OUT THE INVENTION

Figure 1A:
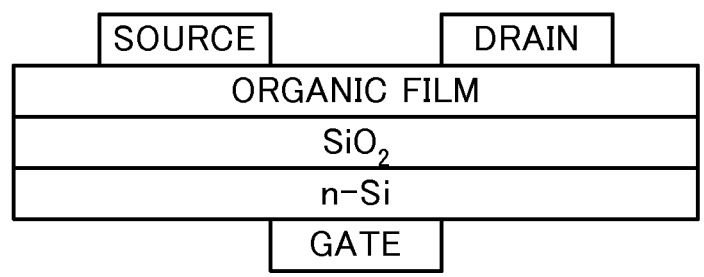
FIG. 1A is a diagram showing a general structure of an FET element produced according to an embodiment and is a cross-sectional view of the FET element.

An explanation will be given of embodiments of a novel compound, a method of producing the compound, an organic semiconductor material and an organic semiconductor device according to the present invention.

<Novel Compound>

A novel compound according to a first embodiment is a compound having a thiophene ring or a selenophene ring bonded with each of two benzene rings contained in naphthalene as represented by following general formula (1), general formula (2), general formula (3) or general formula (4).

[Chemical Formula 7]

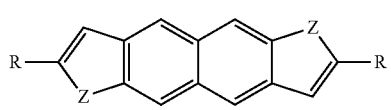
(1)

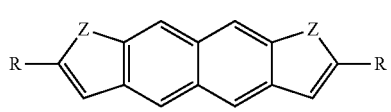
(2)

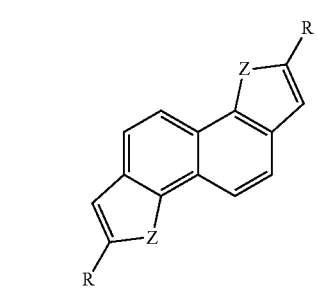
(3)

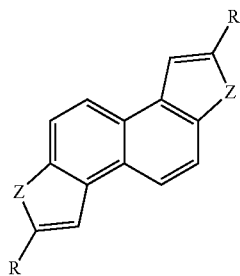
(4)

(where Z represents a sulfur atom or a selenium atom, and R represents a hydrogen atom, an alkyl group or a phenyl group in the above general formulae)

The two R contained in each compound may be the same substituents or the different substituents to each other, but it is preferable that those should be same.

Examples of such alkyl group are straight-chain saturated alkyl groups, such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, and an n-octadecyl group, branched-chain saturated alkyl groups, such as an i-propyl group, an i-butyl group, an s-butyl group, and a t-butyl group, cyclic saturated alkyl groups, such as a cyclo-propyl group, and a cyclo-butyl group, and non-saturated alkyl groups, such as 1-propenyl, 2-propenyl, 1-butynyl, 2-butynyl, and 3-butynyl.

The compounds represented by the above general formulae (1) to (4) have a conjugate system in molecules due to an interaction between π orbitals, and show a strong molecular interaction through a sulfur atom or a selenium atom contained in a thiophene ring or a selenophene ring in each molecule. Accordingly, the compounds represented by the above general formulae (1) to (4) enable carriers to move efficiently, and have a good field mobility. Such compounds can be used as organic semiconductor materials.

A novel compound according to a second embodiment of the present invention is represented by following general formula (5), general formula (6), general formula (7), or general formula (8).

[Chemical Formula 8]

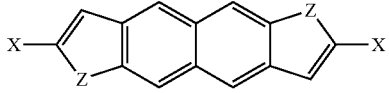
(5)

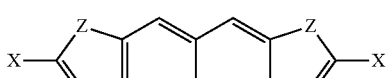
(6)

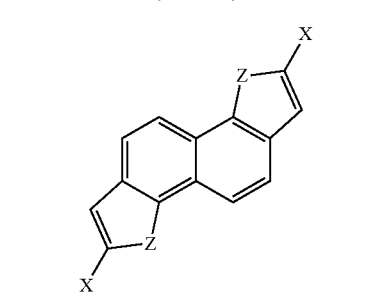
(7)

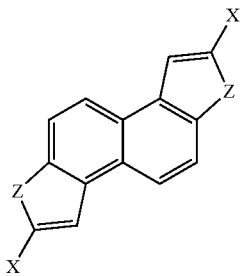

(8)

(where Z represents a sulfur atom or a selenium atom and X represents a halogen atom)

Examples of such a halogen atom are chlorine, bromine, and iodine.

<Production Method of Novel Compound>

Next, an explanation will be given of a production method of the compounds represented by the above general formulae (1), (2), (3), and (4) step by step.

First, dihydroxynaphthalene is reacted with a halogenation agent in order to synthesize dihalogenodihydroxynaphthalene.

Examples of dihydroxynaphthalene are ones having a hydroxy group bonded with each of two benzene rings included in naphthalene. Among such dihydroxynapthalene, 2,6-dihydroxynapthalene, 2,7-dihydroxynaphthalene, or 1,5-dihydroxynaphthalene is preferable.

Conventionally well-known halogenation agent can be used. For example, a bromination agent, such as bromine, N-bromosuccinimide, perbromic pyridinium-hydrobromide or tetraalkylammoniumtribromide, or a chlorination agent, such as chlorine, N-chlolosuccinimide, tetraalkylammoniumtrichloride, thionyl chloride, or sulfuryl chloride can be appropriately used.

Next, the obtained dihalogenodihydroxynaphthalene is reacted with anhydrous trifluoromethanesulfonic acid ($CF_3SO_2$—O—$SO_2CF_3$). The two hydroxy groups contained in dihalogenodihydroxynaphthalene react with anhydrous trifluoromethanesulfonic acid, and are converted into trifluoromethanesulfonateester. As a result, dihalogeno-bis(trifluoromethanesulfonyl)naphthalene is obtained.

Next, the obtained dihalogeno-bis(trifluoromethanesulfonyl)naphthalene is reacted with terminal acetylene compounds. Carbons coupled with trifluoromethanesulfonyl groups are substituted and a dihalogeno-diethynylnaphthalene derivative is obtained.

Examples of terminal acetylene compound are trimethylsilylacethylene ($HC_2Si(CH_3)_3$), phenylacethylene ($C_8H_6$), 1-decyne ($C_{10}H_{18}$).

It is preferable that the reaction of dihalogeno-bis(trifluoromethanesulfonyl)naphthalene with the terminal acetylene compounds should be carried out in a polar solvent which can dissolve dihalogeno-bis(trifluoromethanesulfonyl)naphthalene. By carrying out the reaction in the polar solvent, the trifluoromethanesulfonyl group is selectively substituted with an ethynyl group. Hence, the yield of the dihalogeno-diethynylnaphthalene derivative to be obtained can be improved. By improving the yield of the dihalogeno-diethynylnaphthalene, a waste of reagents to be used can be suppressed, thereby reducing the production cost.

It is preferable that an aprotic polar solvent should be used as the polar solvent. Examples of such aprotic polar solvent are dimethylformamide (DMF), and tetrahydrofuran (THF). The higher the polarity of the aprotic polar solvent is, the higher the yield of the obtained dihalogeno-diethynylnaphthalene derivative becomes. Hence, between such examples, dimethylformamide having the highest polarity is especially preferable to use.

Next, the obtained dihalogeno-diethynylnaphthalene derivative is reacted with sulfide salt or selenide salt. In this process, halogen atoms contained in the dihalogeno-diethynylnaphthalene derivative are substituted with sulfur atoms or selenium atoms. The introduced sulfur atoms or selenium atoms react with the triple bonds of ethynyl group introduced beforehand, and form thiophene rings or selenophene rings. Through such reaction, the compound represented in the formulae (1) to (4) can be obtained.

It is preferable that sulfide metal salt should be used as the sulfide salt, and is more preferable to use sulfide alkali metal salt. For example, sodium-sulfide.9-hydrate ($Na_2S.9H_2O$), sodium-sulfide.5-hydrate ($Na_2S.5H_2O$), sodium-sulfide-anhydride ($Na_2S$), and sodium-hydrosulfide-hydrate ($NaSH.nH_2O$) are preferable. Selenide salt commercially available can be used as the former selenide salt. Alternatively, selenide salt may be induced through conventionally well-known techniques of causing metallic selenium to react with sodium boron hydride, which can be directly used without being isolated.

The amount of sulfide salt used for the reaction can be 1 to 16 mol in general relative to 1 mol of dihalogeno-diethynylnaphthalene derivative. Preferably, 2 to 8 mol, and more preferably, 2 to 5 mol of such sulfide salt is used.

It is fine if the reaction solvent is used or unused, but when the dihalogeno-diethynylnaphthalene derivative to be used is a solid material, it is preferable to use a solvent. In this case, it is preferable that a reaction mixture should contain a solvent having a boiling temperature of equal to or higher than 100° C. When the solvent having the boiling temperature of equal to or higher than 100° C. is contained in the reaction mixture, the reaction temperature can be set to be high, thereby increasing the reaction speed.

Examples of the solvent having the boiling temperature of equal to or higher than 100° C. are amides, such as N-methyl-2-pyrolidone (NMP), N,N-dimethylformamide, and N,N-dimethylacetamide, glycols, such as ethylene glycol, propylene glycol, and polyethylene glycol, and sulfoxide like dimethyl-sulfoxide.

It is appropriate if the amount of above-explained solvent to be used is 0.01 to 100 mol in general relative to 1 mol of dihalogeno-diethynylnaphthalene derivative. Preferably, 0.1 to 80 mol, and more preferably, 20 to 50 mol of such solvent is used.

It is appropriate if the reaction temperature is from −50° C. to 300° C. Preferably, such reaction temperature is from −10° C. to 250° C., and more preferably, from 40° C. to 200° C.

According to the present invention, it is not requisite to add a catalyst, but when the reaction smoothly progresses by adding a catalyst, it is fine if such catalyst is added in each step. An Example of such catalyst that promotes cyclization is metallic halide, such as metal copper or copper chloride (I), copper chloride (II), copper bromide (I), copper bromide (II), copper iodide (I) or copper iodide (II). Preferable one is copper halide, such as metal copper or copper iodide (I) or copper iodide (II).

A target compound is isolated and purified from the reaction mixture through a conventionally well-known technique as needed. In order to obtain a highly pure target compound, for example, sublimation purifying, in particular, vacuum sublimation purifying can be carried out.

A specific explanation will be given of a production method of the compound represented by the general formula (1). When a compound having a trans-form linear structure represented by the general formula (1) is synthesized, 2,6-dihydroxynaphthalene is used as dihydroxynaphthalene. In this case, it is appropriate if a bromination agent is used as the halogenation agent.

In order to obtain the compound with a linear structure represented by the general formula (1), it is necessary to substitute hydrogen atoms bonded with the third and seventh carbons of 2,6-dihydroxynaphthalene with halogen atoms. When a chlorination agent is used as the halogenation agent, the hydrogen atoms bonded with the first and fifth carbons having the high reactivity among hydrogen atoms contained in dihydroxynaphthalene are substituted by chlorine atoms, but hydrogen atoms bonded with the third and seventh carbons are not likely to be substituted.

In contrast, by using the bromination agent like bromine as the halogenation agent, hydrogen atoms bonded with the third and seventh carbons can be substituted with bromine atoms relatively easily. More specifically, first, for example, hydrogen atoms bonded with the first and fifth carbons with a high reactivity are substituted with bromine atoms by the bromination agent. Next, a catalyst that promotes bromination, e.g., iron is added. Under the presence of the catalyst, the bromination agent is successively added multiple times, so that hydrogen atoms bonded with the third and seventh carbons are also substituted, thereby obtaining 1,3,5,7-tetrabromo-2,6-dihydroxynaphthalene.

According to the above-explained scheme, 1,3,5,7-tetrabromo-2,6-dihydroxynaphthalene can be obtained at a high yield (equal to or higher than 50%). It is remarkably high in comparison with the yield of 4% of 1,3,5,7-tetrabromo-2,6-dihydroxynaphthalene reported in "Reaction of Tetrasulfur Tetranitride with Naphthalenols and Related Compounds" (Bull. Chem. Soc. Jpn., Vol. 64, p 68 to 73: Shuntaro Mataka, Kazufumi Takahashi, Youji Ikezaki, Taizo Hatta, Akiyoshi Torii, Masashi Tashiro).

Next, 1,3,5,7-tetrabromo-2,6-dihydroxynaphthalene is subjected to reduction using flake-form tin, etc. Bromine atoms bonded to the first and the fifth are substituted with hydrogen atoms, and 3,7-dibromo-2,6-dihydroxynaphthalene is obtained.

Using this 3,7-dibromo-2,6-dihydroxynaphthalene, reaction with the above-explained anhydrous trifluoromethanesulfonic acid, reaction with a terminal acetylene compound, and reaction with sulfide salt or selenide salt are carried out. Through such individual steps, the compound with a trans-form linear structure represented by the general formula (1) can be selectively obtained. According to this method, as explained above, 1,3,5,7-tetrabromo-2,6-dihydroxynaphthalene can be obtained at a high yield. Hence, reagents can be used efficiently, so that the production cost can be reduced.

Next, a specific explanation will be given of a production method of the compound represented by the general formula (2). When the compound having a cis-form linear structure represented by the general formula (2) is produced, 2,7-dihydroxynaphthalene is used as the dihydroxynaphthalene. It is appropriate if a bromination agent is used as the halogenation agent. When 2,7-dihydroxynaphthalene and the bromination agent like bromine are reacted with each other, because of the eighth steric hindrance, reaction is terminated at tribromide, and 1,3,6-tribromo-2,7-dihydroxynaphthalene is obtained. By performing reduction on it using flake-form tin, 3,6-dibromo-2,7-dihydroxynaphthalene is obtained. Using this 3,6-dibromo-2,7-dihydroxynaphthalene, reaction with the above-explained anhydrous trifluoromethanesulfonic acid, reaction with a terminal acetylene compound, and reaction with sulfide salt or selenide salt are carried out. Through such individual steps, the compound with a cis-form linear structure represented by the general formula (2) can be selectively obtained.

Next, a specific explanation will be given of a production method of the compound represented by the general formula (3). When the compound represented by the general formula (3) is produced, 2,6-dihydroxynaphthalene is used as the dihydroxynaphthalene. It is appropriate if a chlorination agent like chlorine is used as the halogenation agent. When 2,6-dihydroxynaphthalene and the chlorination agent are reacted with each other, 1,5-dichloro-2,6-dihydroxynaphthalene is obtained at the first stage. Using this 1,5-dichloro-2,6-dihydroxynaphthalene, reaction with the above-explained anhydrous trifluoromethanesulfonic acid, reaction with a terminal acetylene compound, and reaction with sulfide salt or selenide salt are carried out. Through such individual steps, the compound represented by the general formula (3) can be selectively obtained.

Next, a specific explanation will be given of a production method of the compound represented by the general formula (4). When the compound represented by the general formula (4) is produced, 1,5-dihydroxynaphthalene is used as the dihydroxynaphthalene. It is appropriate if a bromination agent like bromine is used as the halogenation agent. When 1,5-dihydroxynaphthalene and the bromination agent are reacted with each other, 2,6-dibromo-1,5-dihydroxynaphthalene is obtained at the first stage. Using this 2,6-dibromo-1,5-dihydroxynaphthalene, reaction with the above-explained anhydrous trifluoromethanesulfonic acid, reaction with a terminal acetylene compound, and reaction with sulfide salt or selenide salt are carried out. Through such individual steps, the compound represented by the general formula (4) can be selectively obtained.

Next, an explanation will be given of a production method of the compound represented by each of the general formulae (5) to (8).

According to the production method of the compound of the present invention represented by each of the general formulae (5) to (8), a halogenation agent is added to, for example, the compound which is represented by each of the general formulae (1) to (4), obtained through the above-explained method, and having a hydrogen atom as R. More specifically, first, the compound represented by each of the general formulae (1) to (4) and having a hydrogen atom as R is dissolved in a solvent like tetrahydrofuran (THF). n-BuLi (normal-butyl-lithium), etc., is added to the solvent, and a solution obtained by dissolving the halogenation agent like dibromotetrachloroethane in THF is further dripped therein, so that a target material is obtained.

According to this production method, by adding n-BuLi to the compound represented by each of the general formulae (1) to (4) and having a hydrogen atom as R, hydrogen bonded with adjoining carbon to sulfur or selenium is subjected to abstraction, and lithium salt is produced. When the lithium salt and the halogenation agent react with each other, the substrate is subjected to halogenation. Next, by separating a precipitated solid by, for example, a filter, the compound represented by each of the formulae (5) to (8) can be obtained.

According to this production method, a bromination agent or an iodination agent can be used as the halogenation agent. Appropriate examples of the bromination agent are dibromotetrachloroethane, bromine, perbromicpyridiniumhydrobromide, and tetraalkylammoniumtribromide. Appropriate examples of the iodination agent are iodine, diiodoethane, perfluorohexyl-idodide, and tetraalkylammonium-tri-iodide.

It is appropriate if at least equal to or more than two equivalent weights of n-BuLi is added relative to the compound having a hydrogen atom as R in each of the formulae (1) to (4). This is because the target compound can be obtained efficiently by performing abstraction on two of the hydrogen atoms contained in the compound represented by each of the formulae (1) to (4). When reaction with a portion other than portions desired to be substituted is slow and the possibility of side reaction is little, or when the solubility to the solvent of the compound represented by each of the formulae (1) to (4) is low and reaction does not progress well, extra n-BuLi may be further added.

It is appropriate if the halogenation agent is added at a molar ratio equal to or larger than that of the added n-BuLi. Regarding the blending ratio thereof, for example, approximately 3 to 5 mol of n-BuLi and approximately 10 mol of the halogenation agent may be added relative to 1 mol of the compound represented by each of the formulae (1) to (4).

It is appropriate if the reaction time is 30 minutes to one hour, but the reaction time can be shorter than 30 minutes if it is a sufficient time to complete the abstraction reaction of hydrogen by n-BuLi.

According to the production method of the present invention, halogenation by halogen-lithium substitution reaction using n-BuLi was explained as an example, and the halogenation method is not limited to this example. Other conventionally well-known techniques like a technique of using proton abstraction agent can be applied.

<Organic Semiconductor Material>

Next, an explanation will be given of an embodiment of an organic semiconductor material according to the present invention. The organic semiconductor material of the present invention contains equal to or more than one kind of the compounds represented by the general formula (1), (2), (3) or (4).

The compound represented by the general formula (1), (2), (3) or (4) has a naphthalene-thiophene skeleton or a naphthalene-selenophene skeleton. This compound has a conjugate system in individual molecules due to an interaction between π orbitals, and shows a strong molecular interaction through a sulfur atom or a selenium atom contained in a thiophene ring or a selenophene ring in each molecule. Accordingly, carriers can move efficiently. As a result, the compound of the present invention has a good field mobility, so that it can be used as an organic semiconductor material.

It is fine if the organic semiconductor material contains only one kind of the compound represented by the general formulae (1) to (4), or may contain equal to or more than two kinds of those. Moreover, as long as the characteristics of the compounds represented by the general formulae (1) to (4) are not deteriorated, other materials may be contained. Furthermore, dopants may be doped through a conventionally well-known technique in order to adjust the filed mobility.

<Organic Semiconductor Device>

Next, an explanation will be given of an embodiment of an organic semiconductor device according to the present invention. The organic semiconductor device of the present invention comprises the organic semiconductor material containing at least one kind of the compounds represented by the general formula (1), (2), (3) or (4). Examples of such organic semiconductor device are a thin-film transistor having an organic semiconductor layer, and a light emitting device having either one of or both of organic carrier transport layer and light emitting layer.

Conventionally well-known materials and structures can be applied to the organic semiconductor device of the present invention other than the use of the organic semiconductor material of the present invention, and such conventionally well-known materials and structures are not limited to any particular ones.

How to produce the organic semiconductor device is not limited to any particular one, and various conventionally well-known techniques can be applied. The organic semiconductor material has a solubility which is low on some level, so that when application of a coating technique is difficult, the organic semiconductor device can be produced through a vacuum vapor deposition technique.

According to the organic semiconductor device of the present invention, the organic semiconductor material is used instead of silicon, so that the production process that needs a cost requisite when silicon is used becomes unnecessary. Hence, the semiconductor device can be produced at a low cost.

Moreover, because the organic semiconductor material is used, in comparison with devices using silicon, the organic semiconductor device of the present invention has a good mechanical flexibility and is light-weighted. Hence, the organic semiconductor device of the present invention can be applied to a light-weighted display, a smart tag, etc.

EXAMPLES

The compound of the present invention and the production method thereof will be explained through specific examples below.

First Example

An explanation will be given of synthesis of the compound represented by the general formula (1) and having the liner structure. Note that the structure of the compound is set through $^1$H NMR ($^1$H Nuclear Magnetic Resonance spectrum) and EIMS (mass spectrography spectrum). The apparatuses used for measurement of respective spectra are as follows:

$^1$H-NMR: JEOL Lambda 400 spectrometer
: JEOL EX-270 spectrometer
EIMS: Shimadzu QP-5050A Those apparatuses were also used in other examples to be discussed later.

An explanation will be given of synthesis of naphtho[2,3-b:6,7-b']dithiophene step by step.

Synthesis of
1,3,5,7-tetrabromo-2,6-dihydroxynaphthalene 2,6-dihydroxynaphthalene (2 g, 12.5 mol) was dissolved in acetic acid (60 ml). The acetic acid was used as a solvent. Bromine (2.6 ml. 50.7 mol) was dripped in the solution, and reaction was carried out under a reflux temperature (120° C. to 125° C.).

As is explained in the embodiment for carrying out the present invention, in this stage, first and fifth hydrogen atoms with a high reactivity among hydrogen atoms contained in 2,6-dihydroxynaphthalene were substituted by bromine atoms, and 1,5-dibromo-2,6-dihydroxynaphthalene was merely produced. In order to obtain naphthodithiophene having a linear structure at last, it was further necessary to substitute the third and seventh hydrogen atoms with bromine.

Next, bromine (2.6 ml) was further dripped into the reaction solution by five times at total, and iron powders (50 mg, 1.3 mol) as a catalyst were added thereto, and reaction was caused for 76 hours.

Next, the reaction solution was cooled to a room temperature, and pure water (50 ml) was added thereto. A precipitated solid was separated and collected by filtering. This solid substance was rinsed by acetone, dried under a reduced pressure condition, thereby obtaining a rough product.

The obtained rough product was caused to be recrystallized using 1,4-dioxane as a solvent, and purified. Accordingly, 1,3,5,7-tetrabromo-2,6-dihydroxynaphthalene (3.0 g, yield: 51%) with colorless needle crystals was obtained.

As explained above, by dripping bromine several times and by adding iron powders as a catalyst, 1,3,5,7-tetrabromo-2,6-dihydroxynaphthalene was synthesized at a high yield.

The reaction formula of the above-explained reaction is as follow.

[Chemical Formula 9]

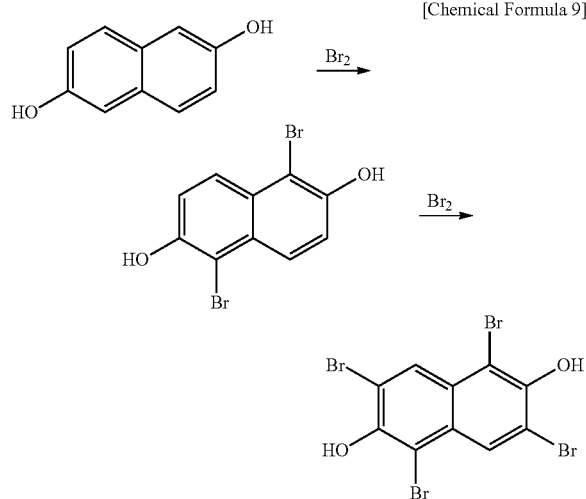

Various spectrum data of the obtained 1,3,5,7-tetrabromo-2,6-dihydroxynaphthalene are indicated below.

$^1$H-NMR (270 MHz, CDCl$_3$) δ6.18 (s, 2H, OH), 8.31 (s, 2H, ArH); EIMS (70 eV) m/z=476 (M$^+$)

Synthesis of 3,7-dibromo-2,6-dihydroxynaphthalene 1,3,5,7-tetrabromo-2,6-dihydroxynaphthalene (1.0 g, 2.1 mmol) was dissolved in acetic acid (20 ml). After flake-form tin (499 mg, 4.2 mmol) was added to the solution, the solution was stirred for 62 hours under a reflux temperature in order to cause a reaction.

Next, the reaction solution was cooled to a room temperature, and pure water (20 ml) was added thereto. A precipitated solid was separated and collected by filtering. This solid substance was dried under a reduced pressure condition, thereby obtaining a white solid of 3,7-dibromo-2,6-dihydroxynaphthalene (530 mg, 79%).

The reaction formula of the above-explained reaction is as follow.

[Chemical Formula 10]

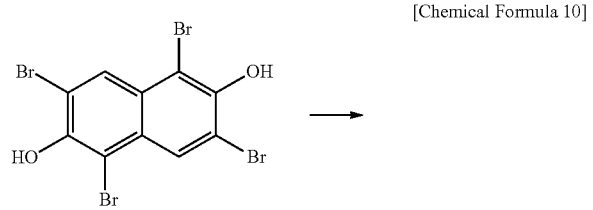

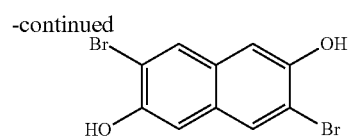

Various spectrum data of the obtained 3,7-dibromo-2,6-dihydroxynaphthalene are indicated below.

$^1$H-NMR (400 MHz, CDCl$_3$) δ5.58 (s, 2H, OH), 7.25 (s, 2H, ArH), 7.89 (s, 2H, ArH); EIMS (70 eV) m/z=318 (M$^+$)

Synthesis of 3,7-dibromo-2,6-bis(trifluoromethanesulfonyl)naphthalene

Under a nitrogen atmosphere, 3,7-dibromo-2,6-dihydroxynaphthalene (636 mg, 2.0 mmol) and pyridine (1.0 ml, 12 mmol) were dissolved in methylene chloride (20 ml).

Anhydrous trifluoromethanesulfonate acid (0.7 ml, 4.4 mmol) was slowly added to the solution in an ice bath. It was stirred for 15 hours and 30 minutes at a room temperature, and pure water (10 ml) and 1N hydrochloric acid (10 ml) were added.

Next, the reaction solution was subjected to extraction using methylene chloride (20 ml). This extraction was performed three times through the same procedures. Thereafter, an organic phase was rinsed by a saturated saline solution (20 ml). This rinsing was performed three times through the same procedures.

Water contained in the organic phase was eliminated using anhydrous magnesium sulfate, and then the solvent was distilled under a pressure reduction condition, thereby obtaining a rough product. The rough product was separated and purified through a silica-gel column chromatography (Rf of target=0.95. Note that Rf represents the same Rf value of a target under a condition of each silica-gel column chromatography if not otherwise mentioned) having methylene chloride as a moving phase, thereby obtaining a white solid of 3,7-dibromo-2,6-bis(trifluoromethanesulfonyl)naphthalene (970 mg, yield: 84%).

The reaction formula of the above-explained reaction is as follow.

[Chemical Formula 11]

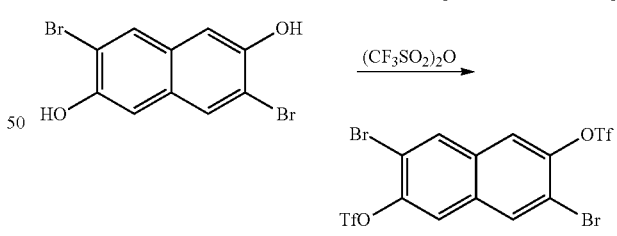

Various spectrum data of the obtained 3,7-dibromo-2,6-bis(trifluoromethanesulfonyl)naphthalene are indicated below.

$^1$H-NMR (270 MHz, CDCl$_3$) δ7.14 (s, 2H, ArH), 8.25 (s, 2H, ArH); EIMS (70 eV) m/z=582 (M$^+$)

Synthesis of 2,6-dibromo-3,7-bis(trimethylsilylethynyl)naphthalene

Under a nitrogen atmosphere, 3,7-dibromo-2,6-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and trimethylsilylacetylene (0.28 ml, 2.0 mmol) as a reagent were added to the solution. It was stirred for 11 hours at a room temperature, and pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product. The rough product was separated and purified through a silica-gel column chromatography (Rf=0.2) having hexane as a moving phase, thereby obtaining a white solid of 2,6-dibromo-3,7-bis(trimethylsilylethynyl)naphthalene (162 mg, yield: 34%).

The reaction formula of the above-explained reaction is as follow.

[Chemical Formula 12]

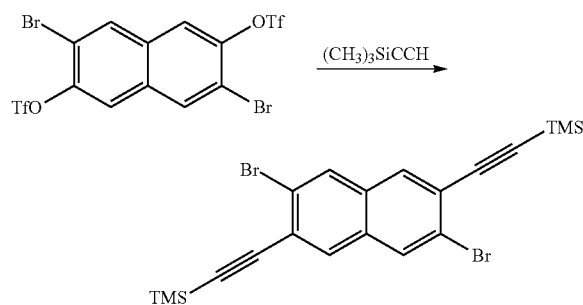

Various spectrum data of the obtained 2,6-dibromo-3,7-bis(trimethylsilylethynyl)naphthalene are indicated below.

$^1$H-NMR (270 MHz, CDCl$_3$) δ0.29 (s, 18H, TMS), 7.87 (s, 2H, ArH), 7.97 (s, 2H, ArH); EIMS (70 eV) m/z=478 (M$^+$)

Synthesis of naphtho[2,3-b:6,7-b']dithiophene

Under a nitrogen atmosphere, Na$_2$S.9H$_2$O (101 mg, 0.42 mmolmmol) was suspended in N-methyl-2-pyrolidone (NMP) (3 ml), and the suspension was stirred for 15 minutes.

2,6-dibromo-3,7-bis(trimethylsilylethynyl)naphthalene (50 mg, 0.1 mmol) was added to the suspension, and the suspension was stirred for 10 hours at a temperature of 190° C.

Next, the suspension was cooled to a room temperature, and poured in a saturated ammonium chloride water solution (20 ml). A precipitated solid was separated and collected by filtering.

This solid substance was separated and purified through a silica-gel column chromatography (Rf=0.95) having hexane as a moving phase, thereby obtaining an orange solid of naphtho[2,3-b:6,7-b']dithiophene (26 mg, yield: 100%).

The reaction formula of the above-explained reaction is as follow.

[Chemical Formula 13]

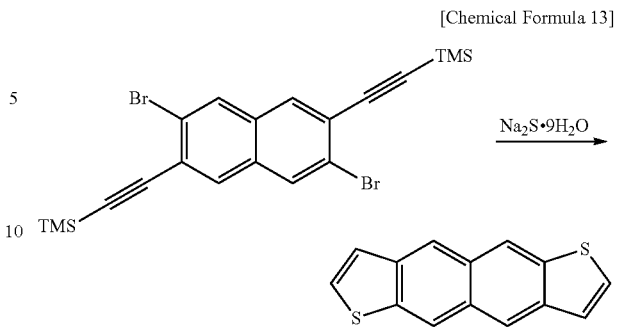

Various spectrum data of the obtained naphtho[2,3-b:6,7-b']dithiophene are indicated below.

$^1$H-NMR (270 MHz, CDCl$_3$) δ7.43 (d, 2H, J=5.8 Hz, ArH), 7.51 (d, 2H, J=5.8 Hz, ArH), 8.41 (s, 2H, ArH), 8.52 (s, 2H, ArH); EIMS (70 eV) m/z=240 (M$^+$); mp>300° C.

Second Example

Next, an explanation will be given of synthesis of 2,7-diphenylnaphto[2,3-b:6,7-b']dithiophene step by step.

Synthesis of 2,6-dibromo-3,7-bis(phenylethynyl)naphthalene

Using 3,7-dibromo-2,6-bis(trifluoromethanesulfonyl)naphthalene synthesized through the above-explained method, 2,6-dibromo-3,7-bis(phenylethynyl)naphthalene was synthesized through the following procedures.

Under a nitrogen atmosphere, 3,7-dibromo-2,6-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and phenylacetylene (0.22 ml, 2.0 mmol) as a reagent were added to the solution, and the solution was stirred for 11 hours at a room temperature in order to let it reacted. Thereafter, pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.1) having hexane as a moving phase, thereby obtaining a white solid of 2,6-dibromo-3,7-bis(phenylethynyl)naphthalene (397 mg, yield: 82%).

The reaction formula of the above-explained reaction is as follow.

[Chemical Formula 14]

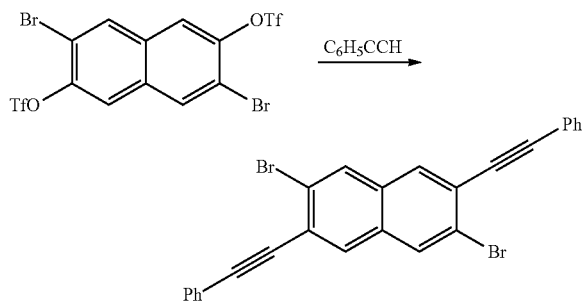

Various spectrum data of the obtained 2,6-dibromo-3,7-bis(phenylethynyl)naphthalene are indicated below.

$^1$H-NMR (400 MHz, CDCl$_3$) δ7.39-7.41 (m, 6H, ArH), 7.62-7.64 (m, 4H, ArH), 7.97 (s, 2H, ArH), 8.07 (s, 2H, ArH); EIMS (70 eV) m/z=486 (M$^+$)

Synthesis of 2,7-diphenylnaphto[2,3-b:6,7-b']dithiophene

Under a nitrogen atmosphere, Na$_2$S.9H$_2$O (202 mg, 0.42 mmol) was suspended in NMP (3 ml), and the suspension was stirred for 15 minutes.

2,6-dibromo-3,7-bis(phenylethynyl)naphthalene (100 mg, 0.2 mmol) obtained beforehand was added to the suspension, and the suspension was stirred for 10 hours at a temperature of 190° C.

The reaction solution was cooled to a room temperature, and poured in a saturated ammonium chloride water solution (20 ml). A precipitated yellow solid (75 mg, yield: 96%) was separated and collected by filtering.

The yellow solid substance was sublimated and purified, thereby obtaining 2,7-diphenylnaphto[2,3-b:6,7-b']dithiophene (25 mg, yield: 32%).

The reaction formula of the above-explained reaction is as follow.

[Chemical Formula 15]

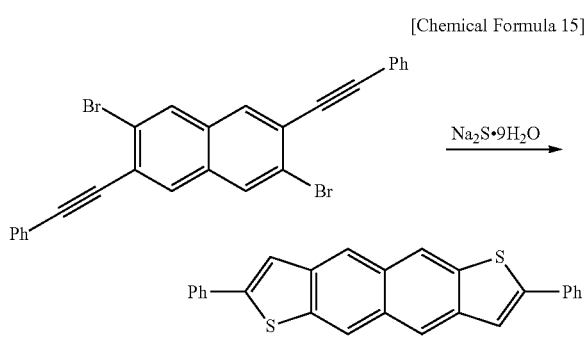

Various spectrum data of the obtained 2,7-diphenylnaphto[2,3-b:6,7-b']dithiophene are indicated below. Note that 2,7-diphenylnaphto[2,3-b:6,7-b']dithiophene was hardly-soluble, which made $^1$H-NMR measurement unable.

EIMS (70 eV) m/z=392 (M$^+$)

Third Example

Next, an explanation will be given of synthesis of 2,7-dioctylnaphto[2,3-b:6,7-b']dithiophene step by step.

Synthesis of 2,6-dibromo-3,7-di(decyne-1-yl)naphthalene

Using 2,6-dibromo-3,7-bis(trifluoromethanesulfonyl)naphthalene synthesized through the above-explained method, 2,6-dibromo-3,7-di(decyne-1-yl)naphthalene was synthesized through the following procedures.

Under a nitrogen atmosphere, 2,6-dibromo-3,7-bis(trifluoromethanesulfonyl)naphthalene (493 mg, 1.0 mmol) was dissolved in DMF (7 ml) and diisopropylamine (0.42 ml. 3.0 mmol). The solution was degassed for 30 minutes.

Pd(PPh$_3$)$_2$Cl$_2$ (70 mg, 0.1 mmol, 10 mol %) and CuI (38 mg, 0.1 mmol, 20 mol %) as catalysts, and 1-decyne (0.54 ml, 3.0 mmol) as a reagent were added to the solution, and the solution was stirred for 27 hours at a room temperature in order to let it reacted. Thereafter, pure water (1 ml) and 1N hydrochloric acid (1 ml) were added, and then reaction was terminated.

The reaction solution was subjected to extraction using methylene chloride (10 ml). This extraction was performed three times through the same procedures. Thereafter, an organic phase was rinsed by a saturated saline solution (10 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.3) having hexane as a moving phase, thereby obtaining a white solid of 2,6-dibromo-3,7-di(decyne-1-yl)naphthalene (488 mg, yield: 87%).

The reaction formula of the above-explained reaction is as follow.

[Chemical Formula 16]

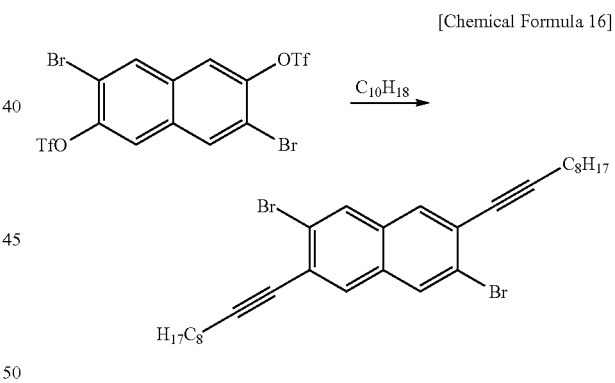

Various spectrum data of the obtained 2,6-dibromo-3,7-di(decyne-1-yl)naphthalene are indicated below.

$^1$H-NMR (270 MHz, CDCl$_3$) δ0.89 (t, 6H, J=7.02 Hz, CH$_2$), 1.27-1.37 (m, 2OH, CH$_2$), 1.61-1.72 (m, 4H, CH$_2$), 2.51 (t, 4H, J=6.62 Hz, CH$_2$), 7.79 (s, 2H, ArH), 7.95 (s, 2H, ArH); EIMS (70 eV) m/z=558 (M$^+$)

Synthesis of 2,7-dioctylnaphto[2,3-b:6,7-b']dithiophene

Under a nitrogen atmosphere, Na$_2$S.9H$_2$O (346 mg, 1.44 mmol) was suspended in NMP (12 ml), and the suspension was stirred for 15 minutes.

2,6-dibromo-3,7-di(decyne-1-yl)naphthalene (200 mg, 0.36 mmol) obtained was added to the suspension, and the suspension was stirred for nine hours at a temperature of 190° C.

The reaction solution was cooled to a room temperature, and poured in a saturated ammonium chloride water solution (30 ml). A precipitated solid was separated and collected by filtering.

The solid substance was separated and purified through silica-gel column chromatography (Rf=0.95) having methylene chloride as a moving phase and through recrystallization using chloroform as a solvent, thereby obtaining yellow needle crystals of 2,7-dioctylnaphto[2,3-b:6,7-b'] dithiophene (130 mg, yield: 78%).

The reaction formula of the above-explained reaction is as follow.

[Chemical Formula 17]

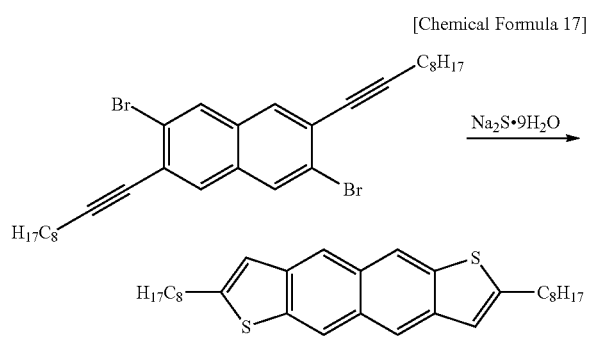

Various spectrum data of the obtained 2,7-dioctylnaphto [2,3-b:6,7-b']dithiophene are indicated below.

$^1$H-NMR (400 MHz, CDCl$_3$) δ0.89 (t, 6H, J=7.4 Hz, CH$_2$), 1.28-1.50 (m, 2OH, CH$_2$), 1.75-1.83 (m, 4H, CH$_2$), 2.92 (t, 4H, J=7.4 Hz, CH$_2$), 7.06 (s, 2H, ArH), 8.16 (s, 2H, ArH), 8.32 (s, 2H, ArH); EIMS (70 eV) m/z=464 (M$^+$); mp 269-271° C.

Fourth Example

Next, a specific explanation will be given of example synthesis of the compound represented by the general formula (2) based on an example.

First, an explanation will be given of synthesis of 2,7-diphenylnaphto[2,3-b:7,6-b']dithiophene step by step.

Synthesis of 1,3,6-tribromo-2,7-dihydroxynaphthalene

Under a nitrogen atmosphere, 2,7-dihydroxynaphthalene (5 g, 31 mmol) was dissolved in acetic acid (150 ml). Note that the acetic acid was used as a solvent.

Bromine (5.3 ml. 103 mmol) was dripped in the solution, and reaction was carried out under a reflux temperature for 41 hours.

The reaction solution was cooled to a room temperature, and pure water (50 ml) was added thereto. A precipitated solid was separated and collected by filtering. This solid substance was rinsed by pure water, dried under a reduced pressure condition, thereby obtaining a white solid of 1,3,6-tribromo-2,7-dihydroxynaphthalene (10 g, yield: 83%).

The reaction formula of the above-explained reaction is as follow.

[Chemical Formula 18]

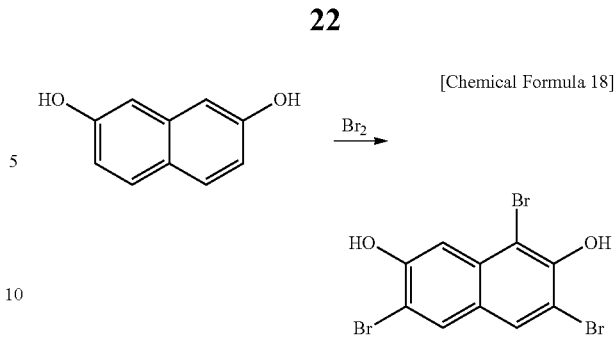

Various spectrum data of the obtained 1,3,6-tribromo-2,7-dihydroxynaphthalene are indicated below.

$^1$H-NMR (270 MHz, CDCl$_3$) δ5.88 (s, 1H, OH), 6.24 (s, 1H, OH), 7.60 (s, 1H, ArH), 7.88 (s, 1H, ArH), 7.89 (s, 1H, ArH); EIMS (70 eV) m/z=396 (M$^+$)

Synthesis of 3,6-dibromo-2,7-dihydroxynaphthalene 1,3,6-triboromo-2,7-dihydroxynaphthalene (5.0 g, 12.6 mmol) was dissolved in acetic acid (20 ml). After flake-form tin (1.6 g, 12.6 mmol) was added to the solution, the solution was stirred for 120 hours under a reflux temperature.

The reaction solution was cooled to a room temperature, and pure water (100 ml) was added thereto. A precipitated solid was separated and collected by filtering. This solid substance was dried under a reduced pressure condition, thereby obtaining a white solid of 3,6-dibromo-2,7-dihydroxynaphthalene (3.4 g, yield: 85%).

The reaction formula of the above-explained reaction is as follow.

[Chemical Formula 19]

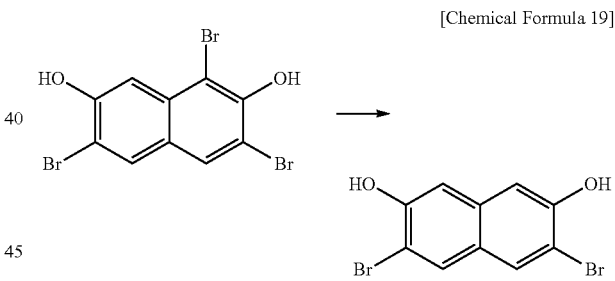

Various spectrum data of the obtained 3,6-dibromo-2,7-dihydroxynaphthalene are indicated below.

$^1$H-NMR (270 MHz, CDCl$_3$) δ5.67 (s, 2H, OH), 7.24 (s, 2H, ArH), 7.87 (s, 2H, ArH); EIMS (70 eV) m/z=318 (M$^+$)

Synthesis of 3,6-dibromo-2,7-bis(trifluoromethane-sulfonyl)naphthalene

Under a nitrogen atmosphere, the obtained 3,6-dibromo-2, 7-dihydroxynaphthalene (3.0 g, 9.4 mmol) was dissolved in pyridine (4.5 ml, 56 mmol) and in methylene chloride (90 ml).

Anhydrous trifluoromethanesulfonate acid (3.3 ml, 21 mmol) was slowly added to the solution in an ice bath. It was stirred for 4 hours and 30 minutes at a room temperature, and pure water (10 ml) and 1N hydrochloric acid (10 ml) were added in order to terminate the reaction.

Next, the reaction solution was subjected to extraction using methylene chloride (20 ml). This extraction was performed three times through the same procedures. Thereafter, an organic phase was rinsed by a saturated saline solution (20 ml). This rinsing was performed three times through the same procedures.

Next, water contained in the organic phase was eliminated using anhydrous magnesium sulfate, and then the solvent was distilled under a pressure reduction condition, thereby obtaining a rough product. The rough product was separated and purified through a silica-gel column chromatography (Rf of target=0.95) having methylene chloride as a moving phase, thereby obtaining a white solid of 3,6-dibromo-2,7-bis(trifluoromethanesulfonyl)naphthalene (3.3 g, yield: 60%).

The reaction formula of the above-explained reaction is as follow.

[Chemical Formula 20]

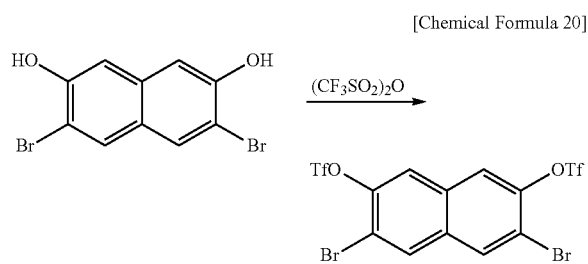

Various spectrum data of the obtained 3,6-dibromo-2,7-bis(trifluoromethanesulfonyl)naphthalene are indicated below.

$^1$H-NMR (400 MHz, CDCl$_3$) δ7.86 (s, 2H, ArH), 8.19 (s, 2H, ArH); EIMS (70 eV) m/z=582 (M$^+$)

Synthesis of 3,6-dibromo-2,7-bis(phenylethynyl)naphthalene

Under a nitrogen atmosphere, 3,6-dibromo-2,7-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and phenylacetylene (0.22 ml, 2.0 mmol) as a reagent were added to the solution. It was stirred for 11 hours at a room temperature, and pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.1) having hexane as a moving phase, thereby obtaining a white solid of 3,6-dibromo-2,7-bis(phenylethynyl)naphthalene (243 mg, yield: 50%).

The reaction formula of the above-explained reaction is as follow.

[Chemical Formula 21]

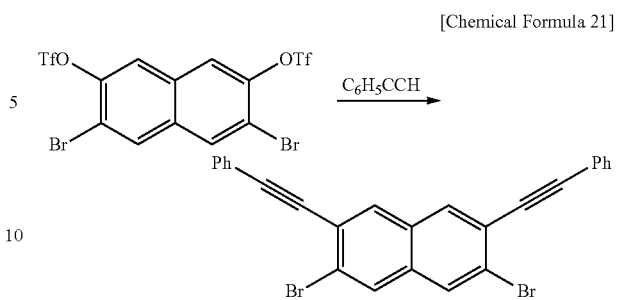

Various spectrum data of the obtained 3,6-dibromo-2,7-bis(phenylethynyl)naphthalene are indicated below.

$^1$H-NMR (270 MHz, CDCl$_3$) δ7.38-7.42 (m, 6H, ArH), 7.62-7.65 (m, 4H, ArH), 8.01 (s, 2H, ArH), 8.03 (s, 2H, ArH); EIMS (70 eV) m/z=486 (M$^+$)

Synthesis of 2,7-diphenylnaphtho[2,3-b:7,6-b']dithiophene

Under a nitrogen atmosphere, Na$_2$S.9H$_2$O (404 mg, 1.68 mmol) was suspended in NMP (12 ml), and the suspension was stirred for 15 minutes.

3,6-dibromo-2,7-bis(phenylethynyl)naphthalene (200 mg, 0.4 mmol) was added to the suspension, and the suspension was stirred for 14 hours at a temperature of 190° C.

The reaction solution was cooled to a room temperature, and poured in a saturated ammonium chloride water solution (20 ml). A precipitated solid was separated and collected by filtering.

This solid substance was rinsed by pure water, ethanol, hexane, methylene chloride, and heated chloroform thereby obtaining 2,7-diphenylnaphtho[2,3-b:7,6-b']dithiophene (73 mg, yield: 45%).

The reaction formula of the above-explained reaction is as follow.

[Chemical Formula 22]

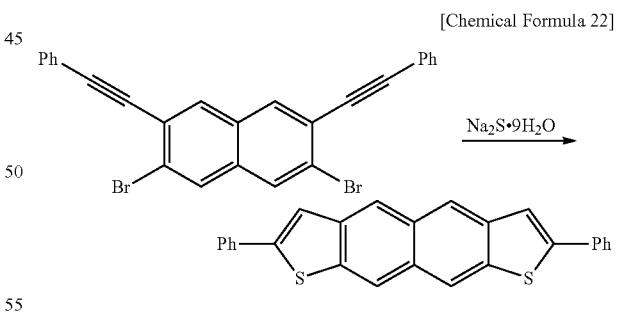

Various spectrum data of the obtained 2,7-diphenylnaphtho[2,3-b:7,6-b']dithiophene are indicated below. Note that 2,7-diphenylnaphtho[2,3-b:7,6-b']dithiophene was hardly soluble, which made NMR measurement unable.

EIMS (70 eV) m/z=392 (M$^+$)

Fifth Example

Next, an explanation will be given of synthesis of 2,7-dioctylenaphto[2,3-b:7,6-b']dithiophene step by step.

Synthesis of 3,6-dibromo-2,7-di(decyne-1-yl)naphthalene

Using 3,6-dibromo-2,7-bis(trifluoromethanesulfonyl) naphthalene synthesized as explained above, 3,6-dibromo-2,7-di(decyne-1-yl)naphthalene was synthesized through the following procedures.

Under a nitrogen atmosphere, 3,6-dibromo-2,7-bis(trifluoromethanesulfonyl)naphthalene (582 mg, 1.0 mmol) was dissolved in DMF (7 ml) and diisopropylamine (7 ml). The solution was degassed for 30 minutes.

$Pd(PPh_3)_2Cl_2$ (70 mg, 0.05 mmol, 10 mol %) and CuI (38 mg, 0.1 mmol, 20 mol %) as catalysts, and 1-decyne (0.36 ml, 2.0 mmol) as a reagent were added to the solution. The solution was stirred for 11 hours at a room temperature in order to let it reacted, and then pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.3) having hexane as a moving phase, thereby obtaining a white solid of 3,6-dibromo-2,7-di(decyne-1-yl)naphthalene (444 mg, yield: 80%).

The reaction formula of the above-explained reaction is as follow.

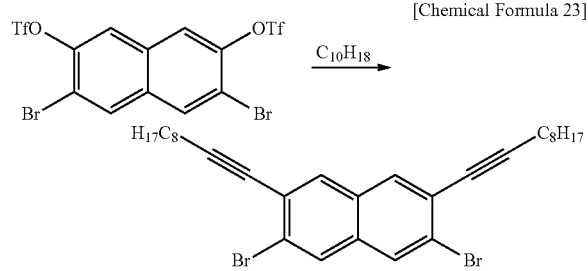

[Chemical Formula 23]

Various spectrum data of the obtained 3,6-dibromo-2,7-di(decyne-1-yl)naphthalene are indicated below.

$^1$H-NMR (270 MHz, CDCl$_3$) δ0.89 (t, 6H, J=6.8 Hz, CH$_2$), 1.27-1.72 (m, 24H, CH$_2$), 2.50 (t, 4H, J=6.9 Hz, CH$_2$), 7.81 (s, 2H, ArH), 7.93 (s, 2H, ArH), EIMS (70 eV) m/z=558 (M$^+$)

Synthesis of 2,7-dioctylenaphtho[2,3-b:7,6-b']dithiophene

Under a nitrogen atmosphere, Na$_2$S.9H$_2$O (346 mg, 1.44 mmol) was suspended in NMP (12 ml), and the suspension was stirred for 15 minutes.

3,6-dibromo-2,7-di(decyne-1-yl)naphthalene (200 mg, 0.36 mmol) was added to the suspension, and the suspension was stirred for 12 hours at a temperature of 190° C. Next, the reaction solution was cooled to a room temperature, and poured in a saturated ammonium chloride water solution (30 ml). A precipitated solid was separated and collected by filtering.

This solid substance was rinsed by pure water and ethanol, thereby obtaining a light yellow solid of 2,7-dioctylenaphtho[2,3-b:7,6-b']dithiophene (168 mg, yield: 100%).

The reaction formula of the above-explained reaction is as follow.

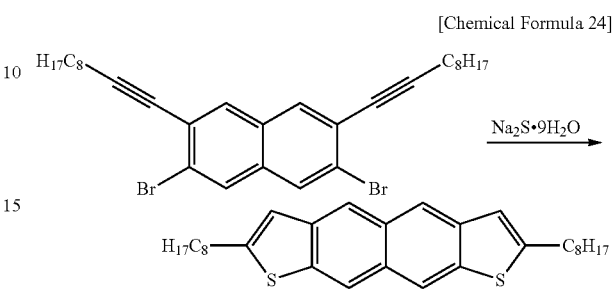

[Chemical Formula 24]

Various spectrum data of the obtained 2,7-dioctylenaphtho[2,3-b:7,6-b']dithiophene are indicated below.

$^1$H-NMR (400 MHz, CDCl$_3$) δ0.88 (t, 6H, J=7.0 Hz, CH$_3$), 1.28-1.81 (m, 24H, CH$_2$), 2.92 (t, 4H, J=7.3 Hz, CH$_2$), 7.05 (s, 2H, ArH), 8.21 (s, 2H, ArH), 8.26 (s, 2H, ArH); EIMS (70 eV) m/z=464 (M$^+$)

Sixth Example

Next, an explanation will be given of synthesis of naphtho[2,3-b:7,6-b']dithiophene step by step.

3,6-dibromo-2,7-bis(trimethylsilylethynyl)naphthalene

Using 3,6-dibromo-2,7-bis(trifluoromethanesulfonyl) naphthalene synthesized as explained above, 3,6-dibromo-2,7-bis(trimethylsilylethynyl)naphthalene was synthesized through the following procedures.

Under a nitrogen atmosphere, 3,6-dibromo-2,7-bis(trifluoromethanesulfonyl)naphthalene (582 mg, 1.0 mmol) was dissolved in DMF (7 ml) and diisopropylamineamine (7 ml). The solution was degassed for 30 minutes.

$Pd(PPh_3)_2Cl_2$ (70 mg, 0.05 mmol, 10 mol %) and CuI (38 mg, 0.1 mmol, 20 mol %) as catalysts, and trimethylsilylacetylene (0.22 ml, 2.0 mmol) as a reagent were added to the solution. It was stirred for 11 hours at a room temperature in order to let it reacted, and then pure water (1 ml) and hexane (20 ml) were added. Next, insoluble solids were filtrated and separated. At this time, high-flow super-cell (registered trademark) was used as a filtration aiding agent.

The filtrate was subjected to extraction using hexane (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.2) having hexane as a moving phase, thereby obtaining a white solid of 3,6-dibromo-2,7-bis(trimethylsilylethynyl)naphthalene (92 mg, yield: 19%).

The reaction formula of the above-explained reaction is as follow.

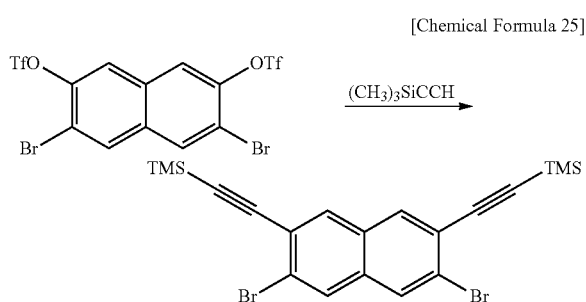

Various spectrum data of the obtained 3,6-dibromo-2,7-bis(trimethylsilylethynyl)naphthalene are indicated below.
$^1$H-NMR (270 MHz, CDCl$_3$) δ0.30 (s, 18H, TMS), 7.90 (s, 2H, ArH), 7.95 (s, 2H, ArH); EIMS (70 eV) m/z=478 (M$^+$)

Synthesis of naphtho[2,3-b:7,6-b']dithiophene

Under a nitrogen atmosphere, Na$_2$S.9H$_2$O (101 mg, 0.42 mmol) was suspended in NMP (3 ml), and the suspension was stirred for 15 minutes.
3,6-dibromo-2,7-bis(trimethylsilylethynyl)naphthalene (50 mg, 0.10 mmol) was added to the suspension, and the suspension was stirred for 12 hours at a temperature of 190° C. It was cooled to a room temperature, and poured in a saturated ammonium chloride water solution (20 ml). A precipitated solid was separated and collected by filtering.
This solid substance was rinsed by pure water, ethanol, and hexane, thereby obtaining a yellow solid of naphtho[2,3-b:7,6-b']dithiophene (73 mg, yield: 45%).
The reaction formula of the above-explained reaction is as follow.

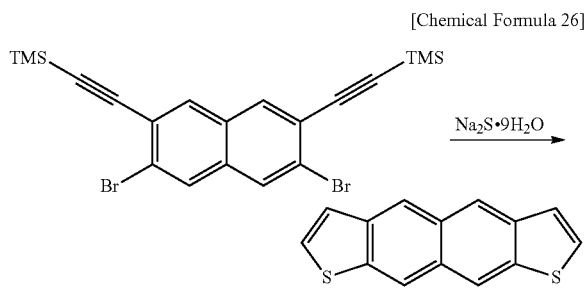

Various spectrum data of the obtained naphtho[2,3-b:7,6-b']dithiophene are indicated below.
$^1$H-NMR (270 MHz, CDCl$_3$) δ7.43 (d, 2H, J=5.5 Hz, ArH), 7.50 (d, 2H, J=5.5 Hz, ArH), 8.45 (s, 2H, ArH), 8.47 (s, 2H, ArH); EIMS (70 eV) m/z=240 (M$^+$)

Seventh Example

Next, a specific explanation will be given of example synthesis of the compound represented by the general formula (3) based on an example.
First, an explanation will be given below of synthesis of naphtho[1,2-b:5,6-b']dithiophene step by step.

Synthesis of 1,5-dichloro-2,6-dihydroxynaphthalene

Under a nitrogen atmosphere, 2,6-dihydroxynaphthalene (3.0 g, 18.7 mmol) was dissolved in acetic acid (90 ml). Note that the acetic acid was used as a solvent.

Sulfuryl chloride (3.0 ml, 37.5 mmol) was dripped in the solution, and the solution was stirred for five hours at a room temperature. Next, pure water (50 ml) was added to the reaction solution. A precipitated solid was separated and collected by filtering. This solid substance was dried under a reduced pressure condition, thereby obtaining a white solid of 1,5-dichloro-2,6-dihydroxynaphthalene (3.3 g, yield: 78%).
The reaction formula of the above-explained reaction is as follow.

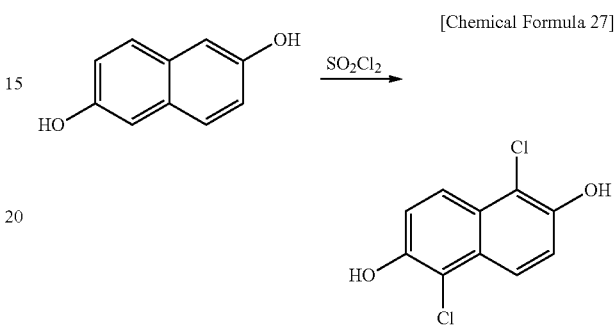

Various spectrum data of the obtained 1,5-dichloro-2,6-dihydroxynaphthalene are indicated below.
$^1$H-NMR (270 MHz, CDCl$_3$) δ5.79 (s, 2H, OH), 7.35 (d, 2H, J=8.9 Hz, ArH), 7.96 (d, 2H, J=8.9 Hz, ArH); EIMS (70 eV) m/z=228 (M$^+$)

Synthesis of 1,5-dichloro-2,6-bis(trifluoromethanesulfonyl)naphthalene

Under a nitrogen atmosphere, 1,5-dichloro-2,6-dihydroxynaphthalene (2.3 g, 10 mmol) and pyridine (4.8 ml, 60 mmol) were dissolved in methylene chloride (100 ml). Note that pyridine was used as an additive in order to eliminate unnecessary materials, and methylene chloride was used as a solvent.
Anhydrous trifluoromethanesulfonate acid (3.6 ml, 22 mmol) was slowly added to the solution in an ice bath. It was stirred for 18 hours at a room temperature, and pure water (10 ml) and 1N hydrochloric acid (10 ml) were added in order to terminate the reaction.
Next, the reaction solution was subjected to extraction using methylene chloride (20 ml). This extraction was performed three times through the same procedures. Thereafter, an organic phase was rinsed by a saturated saline solution (20 ml). This rinsing was performed three times through the same procedures.
Water contained in the organic phase was eliminated using anhydrous magnesium sulfate, and then the solvent was distilled under a pressure reduction condition, thereby obtaining a rough product.
The rough product was separated and purified through a silica-gel column chromatography (Rf of target=0.95) having methylene chloride as a moving phase, thereby obtaining a white solid of 1,5-dichloro-2,6-bis(trifluoromethanesulfonyl)naphthalene (4.9 g, yield: 99%).
The reaction formula of the above-explained reaction is as follow.

[Chemical Formula 28]

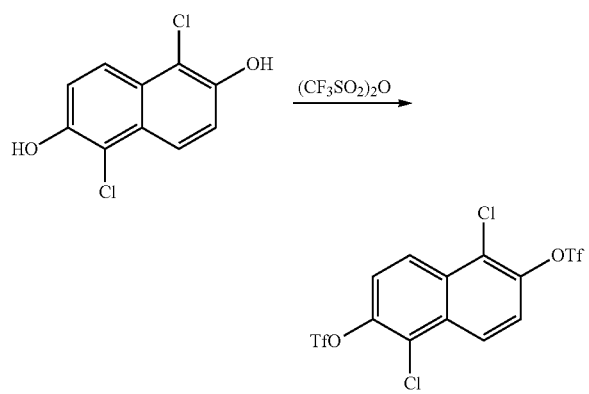

Various spectrum data of the obtained 1,5-dichloro-2,6-bis(trifluoromethanesulfonyl)naphthalene are indicated below.

$^1$H-NMR (270 MHz, CDCl$_3$) δ7.68 (d, 2H, J=9.3 Hz, ArH), 8.40 (d, 2H, J=9.3 Hz, ArH); EIMS (70 eV) m/z=492 (M$^+$)

Synthesis of 1,5-dichloro-2,6-bis(trimethylsilylethynyl)naphthalene

Under a nitrogen atmosphere, 1,5-dichloro-2,6-bis(trifluoromethanesulfonyl)naphthalene (247 mg, 0.5 mmol) and triethylamine (0.21 ml, 1.5 mmol) were dissolved in DMF (5 ml). The solution was degassed for 30 minutes.

Pd(PPh$_3$)$_2$Cl$_2$ (35 mg, 0.05 mmol, 10 mol %) and CuI (19 mg, 0.1 mmol, 20 mol %) as catalysts, and trimethylsilylacetylene (0.21 ml, 15 mmol) as a reagent were added to the solution. It was stirred for 17 hours and 30 minutes at a room temperature, and pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.2) having hexane as a moving phase, thereby obtaining a white solid of 1,5-dichloro-2,6-bis(trimethylsilylethynyl)naphthalene (89 mg, 46%).

The reaction formula of the above-explained reaction is as follow.

[Chemical Formula 29]

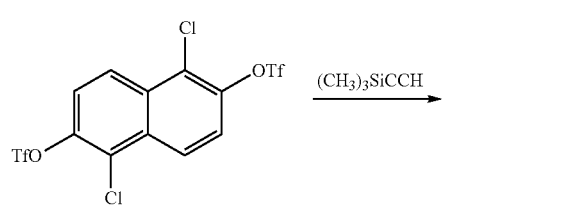

Various spectrum data of the obtained 1,5-dichloro-2,6-bis(trimethylsilylethynyl)naphthalene are indicated below.

$^1$H-NMR (270 MHz, CDCl$_3$) δ0.31 (s, 18H, TMS), 7.61 (d, 2H, J=8.8 Hz, ArH), 8.12 (d, 2H, J=8.8 Hz, ArH); EIMS (70 eV) m/z=388 (M$^+$)

Synthesis of naphtho[1,2-b:5,6-b']dithiophene

Under a nitrogen atmosphere, Na$_2$S.9H$_2$O (615 mg, 2.56 mmol) was suspended in NMP (15 ml), and the suspension was stirred for 15 minutes.

1,5-dichloro-2,6-bis(trimethylsilylethynyl)naphthalene (250 mg, 0.64 mmol) was added to the suspension, and the suspension was stirred for 12 hours at a temperature of 190° C. It was cooled to a room temperature, and poured in a saturated ammonium chloride water solution (50 ml). A precipitated solid was separated and collected by filtering.

This solid substance was separated and purified by a silica-gel column chromatography (Rf=0.2) having hexane as a moving phase, thereby obtaining a white solid of naphtho[1,2-b:5,6-b']dithiophene (139 mg, 90%).

The reaction formula of the above-explained reaction is as follow.

[Chemical Formula 30]

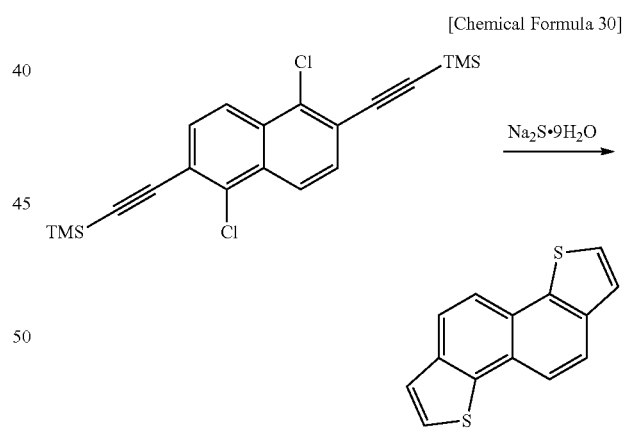

Various spectrum data of the obtained naphtho[1,2-b:5,6-b']dithiophene are indicated below.

$^1$H-NMR (270 MHz, CDCl$_3$) δ7.50 (d, 2H, J=5.3 Hz, ArH), 7.54 (d, 2H, J=5.3 Hz, ArH), 7.95 (d, 2H, J=8.6 Hz, ArH), 8.07 (d, 2H, J=8.6 Hz, ArH); EIMS (70 eV) m/z=240 (M$^+$); mp 150.4-150.8° C.

Eighth Example

Next, an explanation will be given of synthesis of 2,7-diphenylnaphtho[1,2-b:5,6-b']dithiophene step by step.

Synthesis of 1,5-dichloro-2,6-bis(phenylethynyl)naphthalene

Using 1,5-dichloro-2,6-bis(trifluoromethanesulfonyl) naphthalene synthesized as explained above, 1,5-dichloro-2,6-bis(phenylethynyl)naphthalene was synthesized through the following procedures.

Under a nitrogen atmosphere, 1,5-dichloro-2,6-bis(trifluoromethanesulfonyl)naphthalene (493 mg, 1.0 mmol) and triethylamine (0.42 mg, 3.0 mmol) were dissolved in DMF (10 ml). The solution was degassed for 30 minutes.

$Pd(PPh_3)_2Cl_2$ (70 mg, 0.1 mmol, 10 mol %) and CuI (38 mg, 0.1 mmol, 20 mol %) as catalysts, and phenylacetylene (0.33 ml, 3.0 mmol) as a reagent were added to the solution. It was stirred for 27 hours at a room temperature in order to let it reacted, and then pure water (1 ml) and 1N hydrochloric acid (1 ml) were added in order to terminate the reaction.

The reaction solution was subjected to extraction using methylene chloride (10 ml). This extraction was performed three times through the same procedures. Thereafter, an organic phase was rinsed by a saturated saline solution (10 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.2) having hexane as a moving phase, and then rinsed by hexane, thereby obtaining a light yellow solid of 1,5-dichloro-2,6-bis(phenylethynyl) naphthalene (180 mg, yield: 45%).

The reaction formula of the above-explained reaction is as follow.

[Chemical Formula 31]

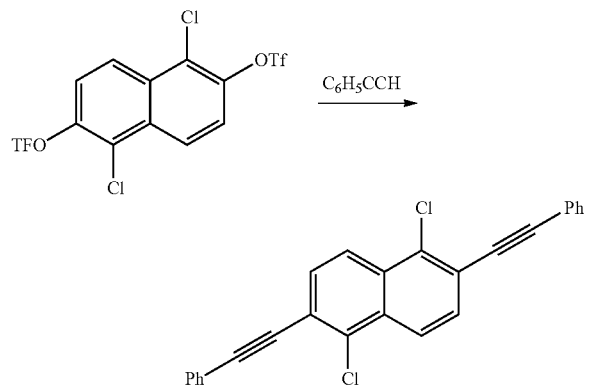

Various spectrum data of the obtained 1,5-dichloro-2,6-bis(phenyethynyl)naphthalene are indicated below.

$^1$H-NMR (270 MHz, $CDCl_3$) δ7.39-7.42 (m, 6H, ArH), 7.63-7.67 (m, 4H, ArH), 7.74 (d, 2H, J=8.6 Hz, ArH), 8.25 (d, 2H, J=8.6 Hz, ArH); EIMS (70 eV) m/z=396 ($M^+$)

Synthesis of 2,7-diphenylnaphtho[1,2-b:5,6-b']dithiophene

Under a nitrogen atmosphere, $Na_2S.9H_2O$ (608 mg, 2.53 mmol) was suspended in NMP (15 ml), and the suspension was stirred for 15 minutes.

1,5-dichloro-2,6-bis(phenylethynyl)naphthalene (250 mg, 0.63 mmol) was added to the suspension, and the suspension was stirred for 12 hours at a temperature of 190° C. The reaction solution was cooled to a room temperature, and poured in a saturated ammonium chloride water solution (50 ml). A precipitated solid was separated and collected by filtering.

The solid substance was subjected to sublimation and purification, thereby obtaining 2,7-diphenylnaphtho[1,2-b:5,6-b']dithiophene (147 mg, 60%).

The reaction formula of the above-explained reaction is as follow.

[Chemical Formula 32]

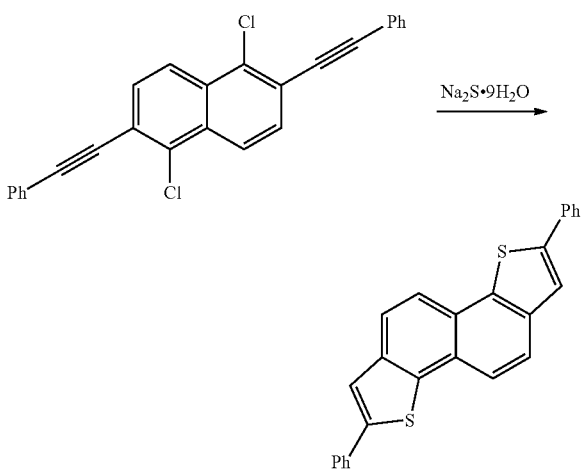

Various spectrum data of the obtained 2,7-diphenylnaphtho[1,2-b:5,6-b']dithiophene are indicated below.

$^1$H-NMR (270 MHz, $CDCl_3$) δ7.34-7.40 (m, 2H, ArH), 7.45-7.57 (m, 4H, ArH), 7.71 (s, 2H, ArH), 7.79-7.82 (m, 4H, ArH), 7.91 (d, 2H, J=8.6 Hz, ArH), 8.05 (d, 2H, J=8.6 Hz, ArH); EIMS (70 eV) m/z=392 ($M^+$)

Ninth Example

Next, an explanation will be given of synthesis of 2,7-dioctylnaphtho[1,2-b:5,6-b']dithiophene step by step.

Synthesis of 1,5-dichloro-2,6-di(decyne-1-yl)naphthalene

Using 1,5-dichloro-2,6-bis(trifluoromethanesulfonyl) naphthalene synthesized as explained above, 1,5-dichloro-2,6-di(decyne-1-yl)naphthalene was synthesized through the following procedures.

Under a nitrogen atmosphere, 1,5-dichloro-2,6-bis(trifluoromethanesulfonyl)naphthalene (493 mg, 1.0 mmol) and triethylamine (0.42 mg, 3.0 mmol) were dissolved in DMF (10 ml). The solution was degassed for 30 minutes.

$Pd(PPh_3)_2Cl_2$ (70 mg, 0.1 mmol, 10 mol %) and CuI (38 mg, 0.1 mmol, 20 mol %) as catalysts, and 1-decyne (0.54 ml, 3.0 mmol) as a reagent were added to the solution. It was stirred for 27 hours at a room temperature in order to let it reacted, and then pure water (1 ml) and 1N hydrochloric acid (1 ml) were added to terminate the reaction.

The reaction solution was subjected to extraction using methylene chloride (10 ml). This extraction was performed three times through the same procedures. Thereafter, an organic phase was rinsed by a saturated saline solution (10 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.3) having hexane as a moving phase, thereby obtaining a white solid of 1,5-dichloro-2,6-di(decyne-1-yl)naphthalene (408 mg, yield: 87%).

The reaction formula of the above-explained reaction is as follow.

[Chemical Formula 33]

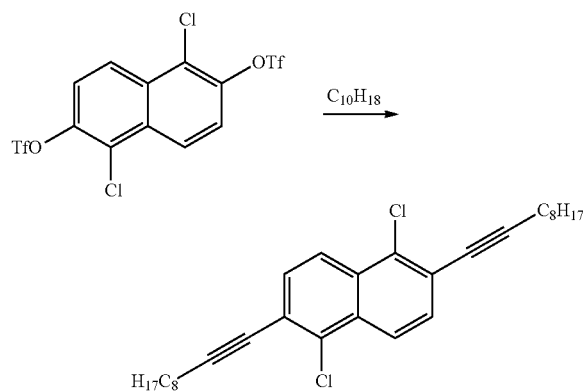

Various spectrum data of the obtained 1,5-dichloro-2,6-di(decyne-1-yl)naphthalene are indicated below.

$^1$H-NMR (270 MHz, CDCl$_3$) δ0.89 (t, 6H, J=7.0, 1.23-1.71 (m, 24H, CH$_2$), 2.53 (t, 4H, J=7.0 Hz, CH$_2$), 7.56 (d, 2H, J=8.5 Hz, ArH), 8.13 (d, 2H, J=8.5 Hz, ArH); EIMS (70 eV) m/z=468 (M$^+$)

Synthesis of 2,7-dioctylnaphtho[1,2-b:5,6-b']dithiophene

Under a nitrogen atmosphere, Na$_2$S.9H$_2$O (204 mg, 0.85 mmol) was suspended in NMP (5 ml), and the suspension was stirred for 15 minutes.

1,5-dichloro-2,6-di(decyne-1-yl)naphthalene (100 mg, 0.21 mmol) was added to the suspension, and the suspension was stirred for 13 hours at a temperature of 190° C. It was cooled to a room temperature, and poured in a saturated ammonium chloride water solution (30 ml). A precipitated solid was separated and collected by filtering.

The solid substance was separated and purified through a silica-gel column chromatography (Rf=0.5) having hexane as a moving phase, thereby obtaining a white solid of 2,7-dioctylnaphtho[1,2-b:5,6-b']dithiophene (147 mg, 60%).

The reaction formula of the above-explained reaction is as follow.

[Chemical Formula 34]

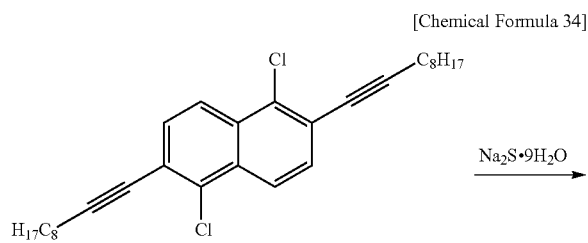

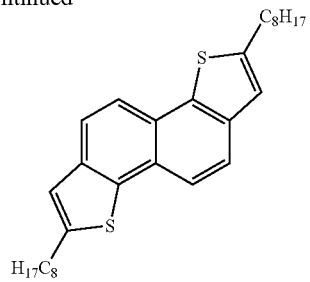

Various spectrum data of the obtained 2,7-dioctylnaphtho[1,2-b:5,6-b']dithiophene are indicated below.

$^1$H-NMR (270 MHz, CDCl$_3$) δ0.88 (t, 6H, J=6.8 Hz, CH$_3$), 1.21-1.83 (m, 24H, CH$_2$), 2.97 (t, 4H, J=7.4 Hz, CH$_2$), 7.14 (s, 2H, ArH), 7.77 (d, 2H, J=8.6 Hz, ArH), 7.91 (d, 2H, J=8.6 Hz, ArH); EIMS (70 eV) m/z=464 (M$^+$); mp 92-93° C.

Tenth Example

Synthesis of naphtho[1,2-b:5,6-b']diselenophene

Under a nitrogen atmosphere, selenium (72 mg, 0.91 mmol) was suspended in ethanol (3 ml), and sodium boron hydride (34 mg, 0.91 mmol) was further added thereto in an ice bath, and the suspension was stirred for 40 minutes.

NMP (10 ml) and 1,5-dichloro-2,6-bis(trimethylsilylethynyl)naphthalene (100 mg, 0.26 mmol) were added to the suspension, and the suspension was stirred for 12 hours at a temperature of 190° C.

The reaction solution was cooled to a room temperature, and poured in a saturated ammonium chloride water solution (50 ml). A precipitated solid was separated and collected by filtering. This solid substance was separated and purified by a silica-gel column chromatography (Rf=0.2) having hexane as a moving phase, thereby obtaining a white solid of naphtho[1,2-b:5,6-b']diselenophene (70 mg, yield: 81%).

The reaction formula of the above-explained reaction is as follow.

[Chemical Formula 35]

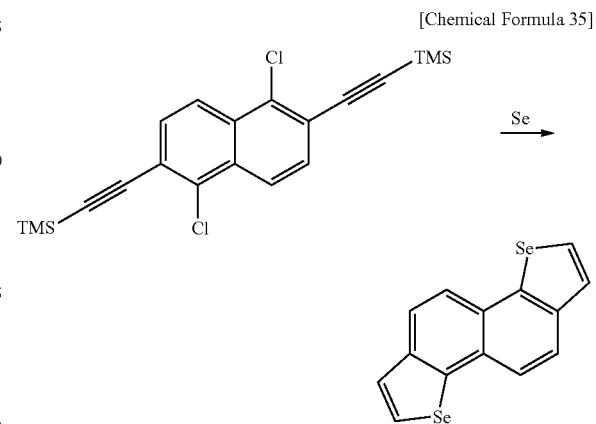

Various spectrum data of the obtained naphtho[1,2-b:5,6-b']diselenophene are indicated below.

$^1$H-NMR (270 MHz, CDCl$_3$) δ7.73 (d, 2H, J=5.8 Hz, ArH), 7.92 (s, 4H, ArH), 8.08 (d, 2H, J=5.9 Hz, ArH), $^{13}$C-NMR (100 MHz, CDCl$_3$) δ123.56, 124.40, 128.37, 128.39, 129.22, 139.95, 142.23; EIMS (70 eV) m/z=336 (M$^+$)

Eleventh Example

Synthesis of 2,7-diphenylnaphtho[1,2-b:5,6-b']diselenophene

Under a nitrogen atmosphere, selenium (141 mg, 1.8 mmol) was suspended in ethanol (4 ml), and then sodium boron hydride (68 mg, 1.8 mmol) was added thereto in an ice bath, and the suspension was stirred for 40 minutes.

NMP (20 ml) and 1,5-dichloro-2,6-bis(phenylethynyl) naphthalene (200 mg, 0.5 mmol) were added to the suspension, and the suspension was stirred for 12 hours at a temperature of 190° C. The reaction solution was cooled to a room temperature, and poured in a saturated ammonium chloride water solution (50 ml). A precipitated solid was separated and collected by filtering.

This solid substance was purified through temperature gradient thermal sublimation, thereby obtaining a light yellow solid of 2,7-diphenylnaphtho[1,2-b:5,6-b']diselenophene (66 mg, yield: 27%).

The reaction formula of the above-explained reaction is as follow.

[Chemical Formula 36]

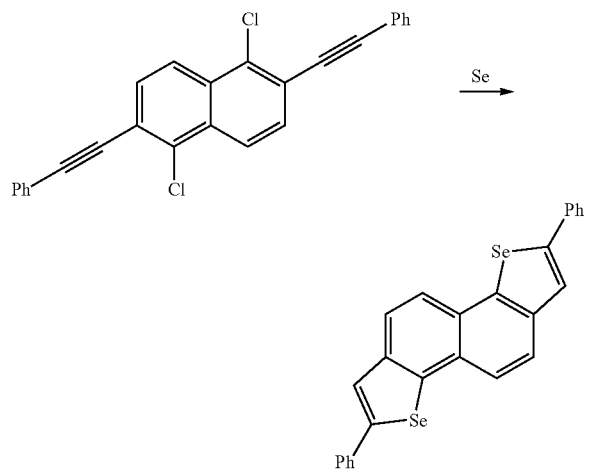

Various spectrum data of the obtained 2,7-diphenylnaphtho[1,2-b:5,6-b']diselenophene are indicated below. Note that 2,7-diphenylnaphtho[1,2-b:5,6-b']diselenophene was hardly soluble, which made $^1$H-NMR measurement unable.
EIMS (70 eV) m/z=488 (M$^+$)

Twelfth Example

Next, a specific explanation will be given of a synthesis example of the compound represented by the general formula (4).

First, an explanation will be given of synthesis of naphtho[2,1-b:6,5-b']dithiophene step by step.

Synthesis of 2,6-dibromo-1,5-dihydroxynaphthalene

Under a nitrogen atmosphere, 1,5-dihydroxynaphthalene (5.0 g, 31 mmol) and a little amount of iodine were dissolved in acetic acid (150 ml). This solution was heated to a temperature of 80° C. Note that acetic acid was used as a solvent.

Bromine (3.2 ml, 62.4 mmol) was dripped in the solution, and reaction was carried out under a reflux temperature for 12 hours. The reaction solution was cooled to a room temperature, and pure water (50 ml) was added thereto. A precipitated solid was separated and collected by filtering. This solid substance was rinsed by pure water, and dried under a reduced pressure condition, thereby obtaining a white solid of 2,6-dibromo-1,5-dihydroxynaphthalene (8.2 g, yield: 83%).

The reaction formula of the above-explained reaction is as follow.

[Chemical Formula 37]

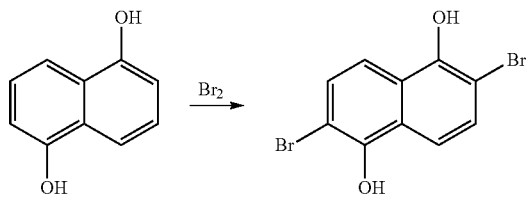

Various spectrum data of the obtained 2,6-dibromo-1,5-dihydroxynaphthalene are indicated below.

$^1$H-NMR (400 MHz, CDCl$_3$) δ5.99 (s, 2H, OH), 7.39 (d, 2H, J=9.4 Hz, ArH), 7.70 (d, 2H, J=9.4 Hz, ArH); EIMS (70 eV) m/z=318 (M$^+$)

Synthesis of 2,6-dibromo-1,5-bis(trifluoromethanesulfonyl)naphthalene

Under a nitrogen atmosphere, 2,6-dibromo-1,5-dihydroxynaphthalene (3.0 g, 9.4 mmol) and pyridine (4.5 ml, 56 mmol) were dissolved in methylene chloride (90 ml). Pyridine was used as an additive in order to eliminate unnecessary materials, and methylene chloride was used as a solvent.

Anhydrous trifluoromethanesulfonate acid (3.3 ml, 21 mmol) was slowly added to the solution in an ice bath. It was stirred for 4 hours and 30 minutes at a room temperature, and pure water (10 ml) and 1N hydrochloric acid (10 ml) were added in order to terminate the reaction.

The reaction solution was subjected to extraction using methylene chloride (20 ml). This extraction was performed three times through the same procedures. Thereafter, an organic phase was rinsed by a saturated saline solution (20 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.95) having methylene chloride as a moving phase, thereby obtaining a white solid of 2,6-dibromo-1,5-bis(trifluoromethanesulfonyl) naphthalene (3.2 g, yield: 58%).

The reaction formula of the above-explained reaction is as follow.

[Chemical Formula 38]

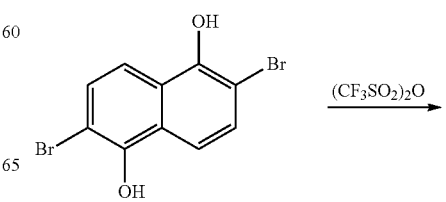

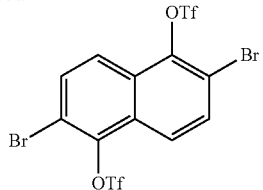

Various spectrum data of the obtained 2,6-dibromo-1,5-bis(trifluoromethanesulfonyl)naphthalene are indicated below.

$^1$H-NMR (270 MHz, CDCl$_3$) δ7.89 (d, 2H, J=9.2 Hz, ArH), 8.03 (d, 2H, J=9.2 Hz, ArH); EIMS (70 eV) m/z=582 (M$^+$)

Synthesis of 2,6-dibromo-1,5-bis(trimethylsilylethynyl)naphthalene

Under a nitrogen atmosphere, 2,6-dibromo-1,5-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and trimethylsilylacetylene (0.28 ml, 2.0 mmol) as a reagent were added to the solution. It was stirred for 11 hours at a room temperature, and pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The obtained rough product was separated and purified through a silica-gel column chromatography (Rf=0.2) having hexane as a moving phase, thereby obtaining a white solid of 2,6-dibromo-1,5-bis(trimethylsilylethynyl)naphthalene (234 mg, yield: 49%).

The reaction formula of the above-explained reaction is as follow.

[Chemical Formula 39]

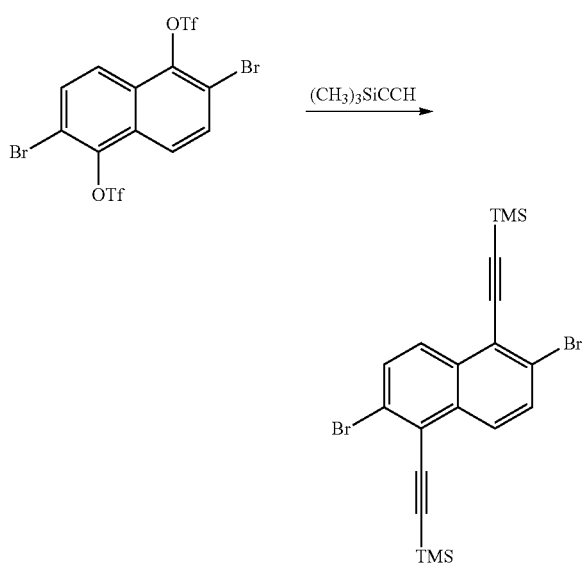

Various spectrum data of the obtained 2,6-dibromo-1,5-bis(trimethylsilylethynyl)naphthalene are indicated below.

$^1$H-NMR (270 MHz, CDCl$_3$) δ0.29 (s, 18H, TMS), 7.71 (d, 2H, J=8.8 Hz, ArH), 8.14 (d, 2H, J=8.8 Hz, ArH); EIMS (70 eV) m/z=478 (M$^+$)

Synthesis of naphtho[2,1-b:6,5-b']dithiophene

Under a nitrogen atmosphere, Na$_2$S.9H$_2$O (202 mg, 0.84 mmol) was suspended in NMP (6 ml), and the suspension was stirred for 15 minutes.

2,6-dibromo-1,5-bis(trimethylsilylethynyl)naphthalene (100 mg, 0.2 mmol) was added to the suspension, and the suspension was stirred for 14 hours at a temperature of 190° C. It was cooled to a room temperature, and poured in a saturated ammonium chloride water solution (20 ml). A precipitated solid was separated and collected by filtering. Thus, naphtho[2,1-b:6,5-b']dithiophene (62 mg) was obtained.

The reaction formula of the above-explained reaction is as follow.

[Chemical Formula 40]

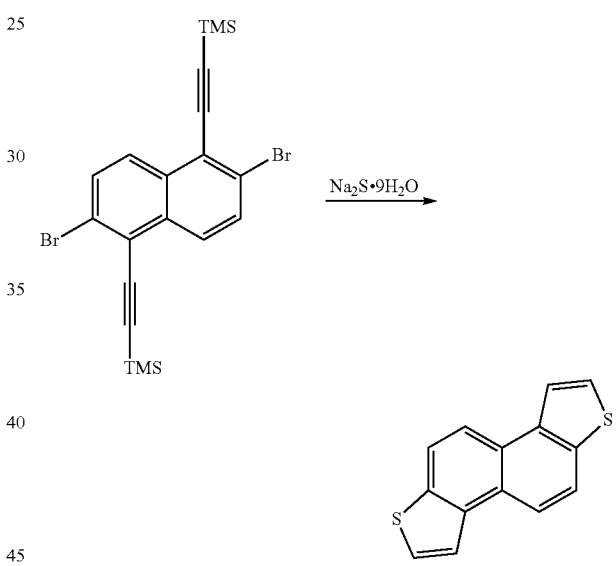

Various spectrum data of the obtained naphtho[2,1-b:6,5-b']dithiophene are indicated below.

$^1$H-NMR (270 MHz, CDCl$_3$) δ7.43 (d, 2H, J=5.4 Hz, ArH), 8.05 (d, 2H, J=5.5 Hz, ArH), 8.05 (d, 2H, J=8.9 Hz, ArH), 8.30 (d, 2H, J=8.9 Hz, ArH); EIMS (70 eV) m/z=240 (M$^+$)

Thirteenth Example

Next, an explanation will be given of synthesis of 2,7-diphenylnaphtho[2,1-b:6,5-b']dithiophene step by step.

Synthesis of 2,6-dibromo-1,5-bis(phenylethynyl)naphthalene

Using 2,6-dibromo-1,5-bis(trifluoromethanesulfonyl)naphthalene synthesized as explained above, 2,6-dibromo-1,5-bis(phenylethynyl)naphthalene was synthesized through the following procedures.

Under a nitrogen atmosphere, 2,6-dibromo-1,5-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and phenylacetylene (0.22 ml, 2.0 mmol) as a reagent were added to the solution. It was stirred for 11 hours at a room temperature in order to let it reacted, and then pure water (1 ml) and 1N hydrochloric acid (1 ml) were added in order to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.1) having hexane as a moving phase, thereby obtaining a white solid of 2,6-dibromo-1,5-bis(phenylethynyl)naphthalene (437 mg, yield: 90%).

The reaction formula of the above-explained reaction is as follow.

[Chemical Formula 41]

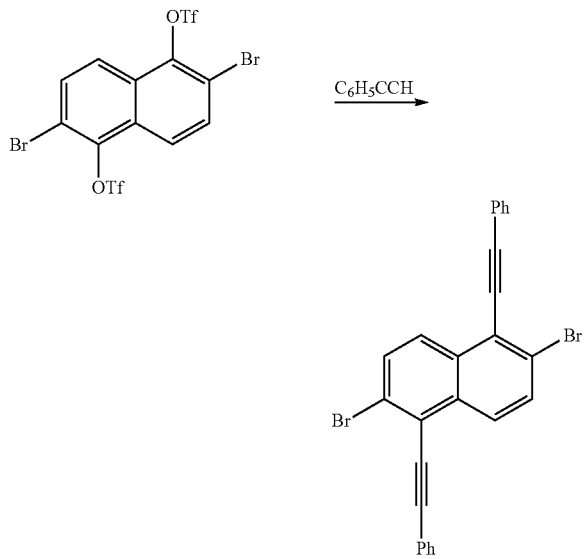

Various spectrum data of the obtained 2,6-dibromo-1,5-bis(phenyethynyl)naphthalene are indicated below.

$^1$H-NMR (270 MHz, CDCl$_3$) δ7.42-7.44 (m, 6H, ArH), 7.69-7.72 (m, 4H, ArH), 7.79 (d, 2H, J=8.9 Hz, ArH), 8.27 (d, 2H, J=8.9 Hz, ArH); EIMS (70 eV) m/z=486 (M$^+$)

Synthesis of
2,7-diphenylnaphtho[2,1-b:6,5-b']dithiophene

Under a nitrogen atmosphere, Na$_2$S.9H$_2$O (404 mg, 1.68 mmol) was suspended in NMP (12 ml), and the suspension was stirred for 15 minutes.

2,6-dibromo-1,5-bis(phenylethynyl)naphthalene (200 mg, 0.4 mmol) was added to the suspension, and the suspension was stirred for 14 hours at a temperature of 190° C. It was cooled to a room temperature, and poured in a saturated ammonium chloride water solution (20 ml). A precipitated solid was separated and collected by filtering, thereby obtaining 2,7-diphenylnaphtho[2,1-b:6,5-b']dithiophene (192 mg).

The reaction formula of the above-explained reaction is as follow.

[Chemical Formula 42]

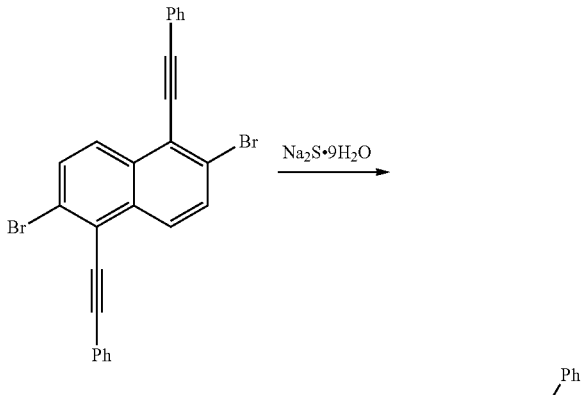

Various spectrum data of the obtained 2,7-diphenylnaphtho[2,1-b:6,5-b']dithiophene are indicated below.

$^1$H-NMR (400 MHz, CDCl$_3$) δ7.39-7.40 (m, 2H, ArH), 7.47-7.51 (m, 4H, ArH), 7.82-7.84 (m, 4H, ArH), 8.01 (d, 2H, J=8.6 Hz, ArH), 7.71 (s, 2H, ArH), 8.05 (d, 2H, J=8.6 Hz, ArH); EIMS (70 eV) m/z=392 (M$^+$)

Fourteenth Example

Next, an explanation will be given of synthesis of 2,7-dioctylnaphtho[2,1-b:6,5-b']dithiophene step by step.

Synthesis of
2,6-dibromo-1,5-di(decyne-1-yl)naphthalene

Using 2,6-dibromo-1,5-bis(trifluoromethanesulfonyl) naphthalene synthesized as explained above, 2,6-dibromo-1,5-di(decyne-1-yl)naphthalene was synthesized through the following procedures.

Under a nitrogen atmosphere, 2,6-dibromo-1,5-bis(trifluoromethanesulfonyl)naphthalene (582 mg, 1.0 mmol) was dissolved in DMF (7 ml) and diisopropylamine (7 ml). The solution was degassed for 30 minutes.

Pd(PPh$_3$)$_2$Cl$_2$ (70 mg, 0.05 mmol, 10 mol %) and CuI (38 mg, 0.1 mmol, 20 mol %) as catalysts, and 1-decyne (0.36 ml, 2.0 mmol) as a reagent were added to the solution. It was stirred for 11 hours at a room temperature in order to let it reacted, and then pure water (1 ml) and 1N hydrochloric acid (1 ml) were added to terminate the reaction.

The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product.

The rough product was separated and purified through a silica-gel column chromatography (Rf=0.2) having hexane as a moving phase, thereby obtaining a white solid of 2,6-dibromo-1,5-di(decyne-1-yl)naphthalene (340 mg, yield: 61%).

The reaction formula of the above-explained reaction is as follow.

[Chemical Formula 43]

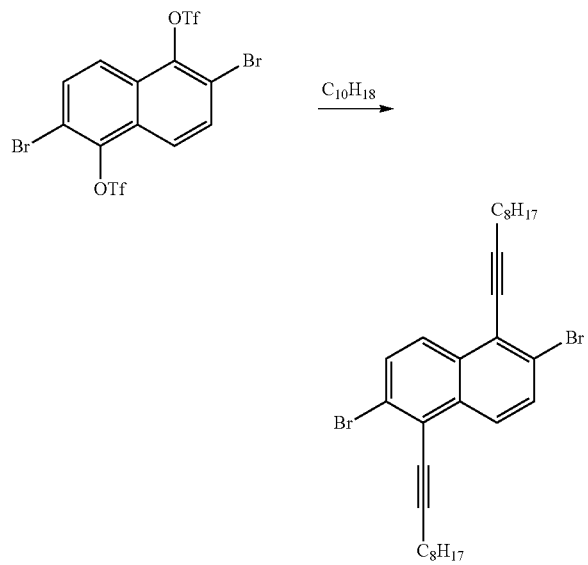

Various spectrum data of the obtained 2,6-dibromo-1,5-di(decyne-1-yl)naphthalene are indicated below.

$^1$H-NMR (270 MHz, CDCl$_3$) δ0.89 (t, 6H, J=7.0, 1.26-1.70 (m, 24H, CH$_2$), 2.62 (t, 4H, J=7.3 Hz, CH$_2$), 7.68 (d, 2H, J=9.4 Hz, ArH), 8.10 (d, 2H, J=9.4 Hz, ArH); EIMS (70 eV) m/z=558 (M$^+$)

Synthesis of
2,7-dioctylnaphtho[2,1-b:6,5-b']dithiophene

Under a nitrogen atmosphere, Na$_2$S.9H$_2$O (404 mg, 1.68 mmol) was suspended in NMP (12 ml), and the suspension was stirred for 15 minutes.

2,6-dibromo-1,5-di(decyne-1-yl)naphthalene (200 mg, 0.4 mmol) was added to the suspension, and the suspension was stirred for 14 hours at a temperature of 190° C. It was cooled to a room temperature, and poured in a saturated ammonium chloride water solution (20 ml). A precipitated solid was separated and collected by filtering, thereby obtaining 2,7-dioctylnaphtho[2,1-b:6,5-b']dithiophene (200 mg, yield: 100%).

The reaction formula of the above-explained reaction is as follow.

[Chemical Formula 44]

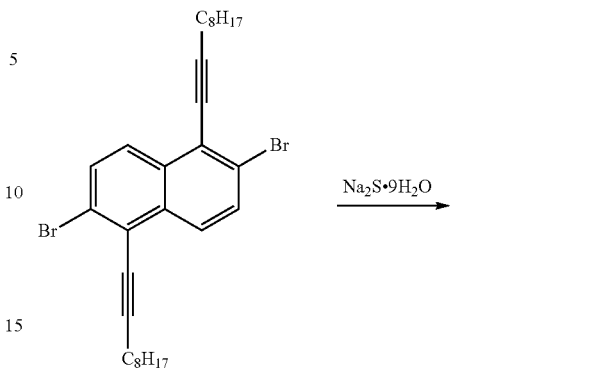

Various spectrum data of the obtained 2,7-dioctylnaphtho[2,1-b:6,5-b']dithiophene are indicated below.

$^1$H-NMR (400 MHz, CDCl$_3$) δ0.88 (t, 6H, J=7.0 Hz, CH$_3$), 1.26-1.70 (m, 24H, CH$_2$), 3.02 (t, 4H, J=7.3 Hz, CH$_2$), 7.68 (s, 2H, ArH), 7.89 (d, 2H, J=8.8 Hz, ArH), 8.12 (d, 2H, J=8.8 Hz, ArH); EIMS (70 eV) m/z=464 (M$^+$)

Fifteenth Example

Next, a specific explanation will be given of an example synthesis of the compound represented by the general formula (5).

Synthesis of
2,7-dibromonaphtho[2,3-b:6,7-b']dithiophene

Under a nitrogen atmosphere, naphtha[2,3-b:6,7-b']dithiophene (50 mg, 0.21 mmol) synthesized in the first example was suspended in THF (10 ml). The suspension was cooled to a temperature of −78° C., and n-BuLi (0.4 ml, 0.63 mmol, 1.59 M) was added thereto. It was stirred for 30 minutes, and the THF solution (3 mL) of 1,2-dibromo-1,1,2,2-tetrachloroethane (150 mg, 0.46 mmol) was dripped therein.

Next, the reaction solution was subjected to temperature rising to a room temperature, stirred for 16 hours, and pure water (1 ml) and 1N hydrochloric acid (1 ml) were added to the reaction solution in order to terminate the reaction. A precipitated solid was collected by filtering, thereby obtaining 2,7-dibromonaphtho[2,3-b:6,7-b']dithiophene (15 mg, yield: 18%).

The reaction formula of the above-explained reaction is as follow.

[Chemical Formula 45]

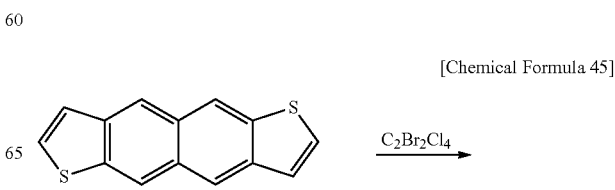

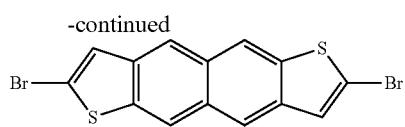

Various spectrum data of the obtained 2,7-dibromonaphtho[2,3-b:6,7-b']dithiophene are indicated below.

$^1$H-NMR (400 MHz, CDCl$_3$) δ7.43 (s, 2H, ArH), 8.22 (s, 2H, ArH), 8.31 (s, 2H, ArH); EIMS (70 eV) m/z=398 (M$^+$)

Sixteenth Example

Next, a specific explanation will be given of an example synthesis of the compound represented by the general formula (7).

Synthesis of 2,7-dibromonaphtho[1,2-b:5,6-b']dithiophene

Under a nitrogen atmosphere, naphtho[1,2-b:5,6-b']dithiophene (50 mg, 0.21 mmol) synthesized in the seventh example was dissolved in THF (5 ml). The solution was cooled to a temperature of −78° C., and n-BuLi (0.4 ml, 0.63 mmol, 1.59 M) was added thereto. It was stirred for 30 minutes, and the THF solution (3 mL) of 1,2-dibromo-1,1,2,2-tetrachloroethane (651 mg, 2 mmol) was dripped therein.

The reaction solution was subjected to temperature rising to a room temperature, stirred for 16 hours, and pure water (1 ml) and 1N hydrochloric acid (1 ml) were added to the reaction solution in order to terminate the reaction. The reaction solution was subjected to extraction using methylene chloride (5 ml). This extraction was performed three times through the same procedures. Thereafter, an organic phase was rinsed by a saturated saline solution (5 ml). This rinsing was performed three times through the same procedures.

Water contained in the organic phase was eliminated using anhydrous magnesium sulfate, and then the solvent was distilled under a pressure reduction condition, thereby obtaining a rough product. The rough product was separated and purified through a silica-gel column chromatography (Rf=0.95) having methylene chloride as a moving phase, thereby obtaining a white solid of 2,7-dibromonaphtho[1,2-b:5,6-b']dithiophene (68 mg, yield: 81%).

The reaction formula of the above-explained reaction is as follow.

[Chemical Formula 46]

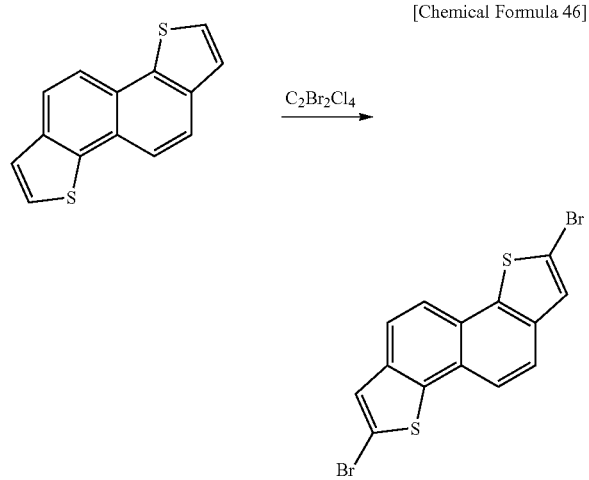

Various spectrum data of the obtained 2,7-dibromonaphtho[1,2-b:5,6-b']dithiophene are indicated below.

$^1$H-NMR (270 MHz, CDCl$_3$) δ7.48 (s, 2H, ArH), 7.80 (d, 2H, J=8.5 Hz, ArH), 7.87 (d, 2H, J=8.5 Hz, ArH); EIMS (70 eV) m/z=398 (M$^+$)

Seventeenth Example

Synthesis of 2,7-diiodenaphtho[1,2-b:5,6-b']dithiophene

Under a nitrogen atmosphere, naphtho[1,2-b:5,6-b']dithiophene (50 mg, 0.21 mmol) synthesized in the seventh example was dissolved in THF (5 ml). The solution was cooled to a temperature of −78° C., and n-BuLi (0.4 ml, 0.63 mmol, 1.59 M) was added thereto. It was stirred for 30 minutes, and the THF solution (3 mL) of iodine (117 mg, 0.46 mmol) was dripped therein.

The reaction solution was subjected to temperature rising to a room temperature, stirred for 10 hours, and pure water (1 ml) and 1N hydrochloric acid (1 ml) were added to the reaction solution in order to terminate the reaction. A precipitated solid was collected by filtering, thereby obtaining a white solid of 2,7-diiodenaphtho[1,2-b:5,6-b']dithiophene (82 mg, yield: 80%).

The reaction formula of the above-explained reaction is as follow.

[Chemical Formula 47]

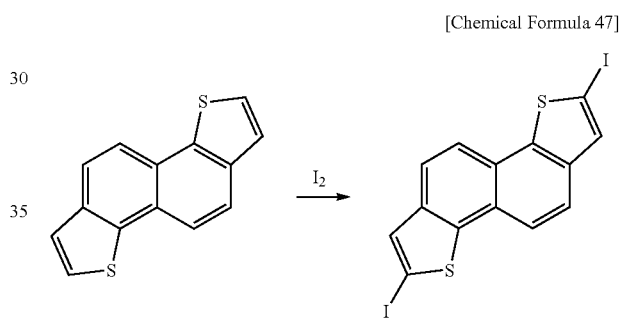

Various spectrum data of the obtained 2,7-diiodenaphtho[1,2-b:5,6-b']dithiophene are indicated below.

$^1$H-NMR (270 MHz, CDCl$_3$) δ7.68 (s, 2H, ArH), 7.82 (d, 2H, J=8.8 Hz, ArH), 7.86 (d, 2H, J=8.8 Hz, ArH); EIMS (70 eV) m/z=492 (M$^+$)

Eighteenth Example

FET Characteristics

FET devices were produced using 2,7-diphenylnaphtho[2,3-b:6,7-b']dithiophene (hereinafter, referred to as a compound A) synthesized in the second example, 2,7-dioctylnaphtho[2,3-b:6,7-b']dithiophene (hereinafter, referred to as a compound B) synthesized in the third example, 2,7-diphenylnaphtho[1,2-b:5,6-b']dithiophene (hereinafter, referred to as a compound C) synthesized in the eighth example, and 2,7-diphenylnaphtho[1,2-b:5,6-b']diselenophene (hereinafter, referred to as a compound D) synthesized in the eleventh example, respectively, and respective FET characteristics were examined.

An FET device using the compound A was produced as follows. First, an SiO$_2$ substrate was cut out with an area of 1 cm by 1 cm. The rear face of the SiO$_2$ substrate was processed by hydrofluoric acid in order to eliminate silica oxidized in air. Next, Au was vacuum vapor deposited on the SiO$_2$ substrate, and a gate electrode was formed. An organic thin-film of the compound A was formed on the front face of the SiO$_2$ substrate by vacuum vapor deposition. Note that SiO$_2$ substrate used was subjected to a surface process using octyltrichlorosilane.

Au was vacuum vapor deposited on the formed organic thin-film of the compound A using a shadow mask, thereby forming a source electrode and a drain electrode.

Figure 1B:
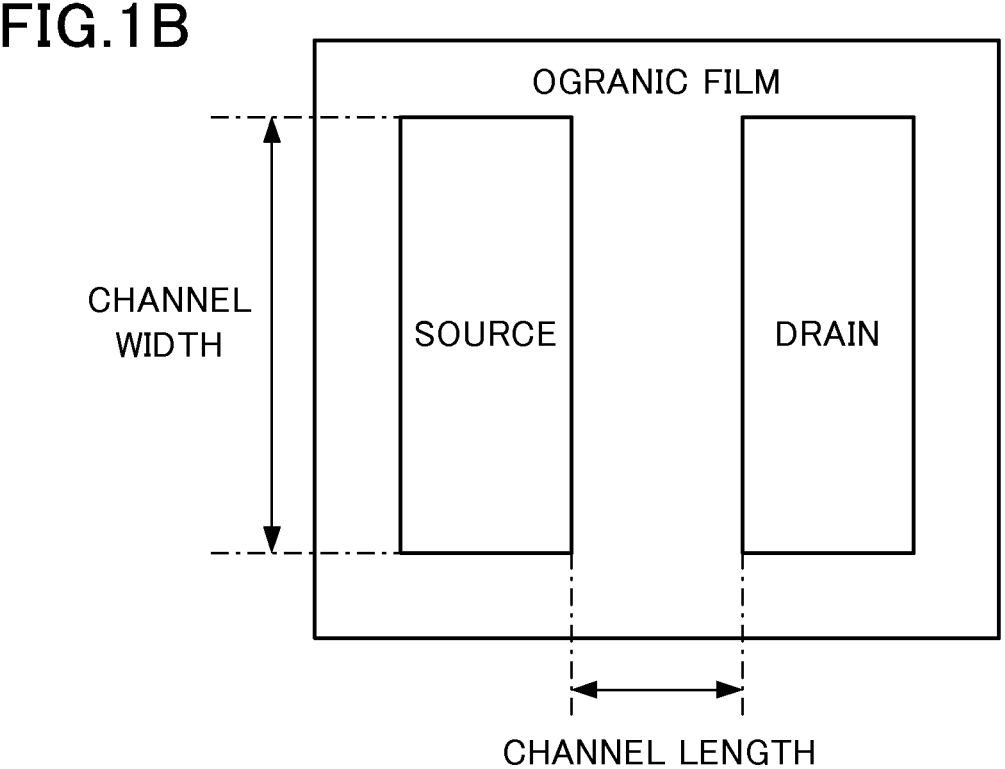
FIG. 1B is a diagram showing a general structure of an FET element produced according to an embodiment and is a plan view of the FET element.

The schematic configuration of the produced FET device is shown in FIG. 1 (FIG. 1A is a cross-sectional view of the FET device, and FIG. 1B is a plan view of the FET device). The FET device produced was a top-contact type. The channel length was 50 µm, and the channel width was 1.5 mm.

An FET device using the compound C and an FET device using the compound D were produced through the same procedures.

Moreover, an FET device using the compound B was produced as follows. First, an SiO$_2$ substrate was cut out with an area of 1 cm by 1 cm. The rear face of the SiO$_2$ substrate was processed by hydrofluoric acid in order to eliminate silica oxidized in air. Next, Au was vacuum vapor deposited on the SiO$_2$ substrate, and a gate electrode was formed. An organic thin-film of the compound B was formed on the front face of the SiO$_2$ substrate through a spin coating technique (an organic thin-film forming condition: 3000 rpm, 30 sec). At this time, the compound B was used as a chloroform solution (concentration: 0.4 wt %).

Au was vacuum vapor deposited on the formed organic thin-film of the compound B using a shadow mask, thereby forming a source electrode and a drain electrode. Note that this FET device had the same configuration, etc., as that of the above-explained other FET devices.

The performance of an FET device depends on an amount of current flowing when a potential is applied across the source electrode and the drain electrode with a potential being applied to the gate electrode. Hence, by measuring the current value, it is possible to check the field mobility which is a characteristic of the FET device. The field mobility can be obtained from an equation (a) representing the electrical characteristics of a carrier kind produced in the organic semiconductor layer upon application of the gate voltage to the SiO$_2$ as an insulator.

$$Id = W\mu C_o (V_g - V_t)^2 / 2L \qquad (a)$$

In the equation (a), Id is a saturated source-drain current value, W is a channel width, Co is a gate electric capacity, $V_g$ is a gate electrode, $V_t$ is a threshold voltage, and L is a channel length. µ is the field mobility (cm$^2$/Vs) of the FET device set upon measurement. Co can be set depending on the dielectric constant of the SiO$_2$ insulator used. W and L can be set depending on the device configuration of the FET device. Id and $V_g$ can be set when the current value of the FET device is measured. $V_t$ can be obtained from Id and $V_g$. By substituting respective values in the equation (a), the field mobility of each gate potential can be calculated. Note that the threshold voltage [$V_t$] was obtained as $V_g$ which was a value of a curve rising when plotted with the square root of −Id being as a Y axis and $V_g$ being as an X axis.

Regarding respective FET devices, in order to check a p-type FET characteristic, a negative gate electrode was applied and respective FET devices were driven in air in order to make an evaluation.

Figure 2A:
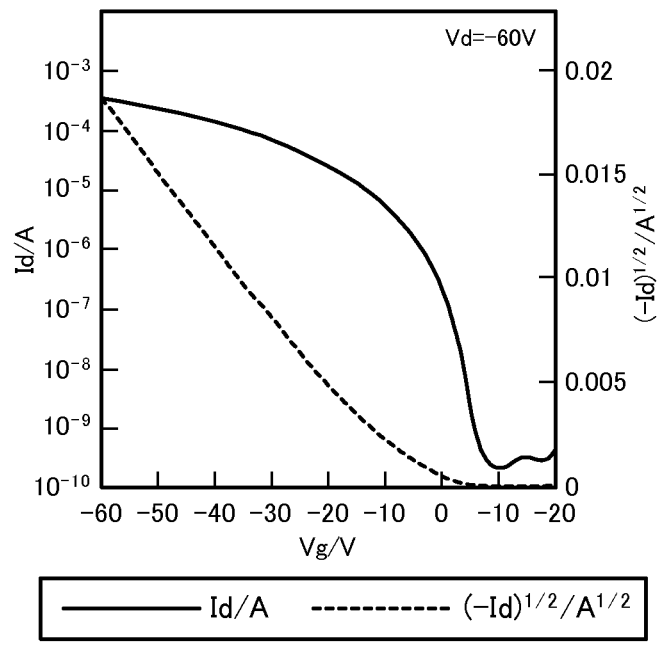
FIG. 2A shows a Vg-Id curve of an FET element produced using a compound A.
Figure 2B:
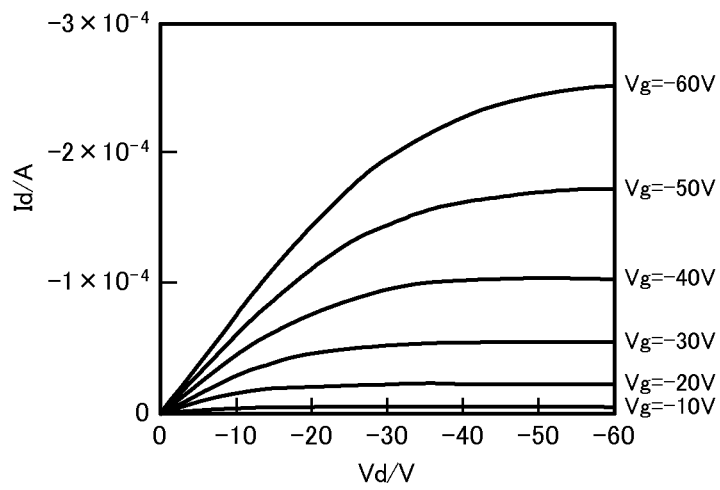
FIG. 2B shows a Vd-Id curve of the FET element.
Figure 3A:
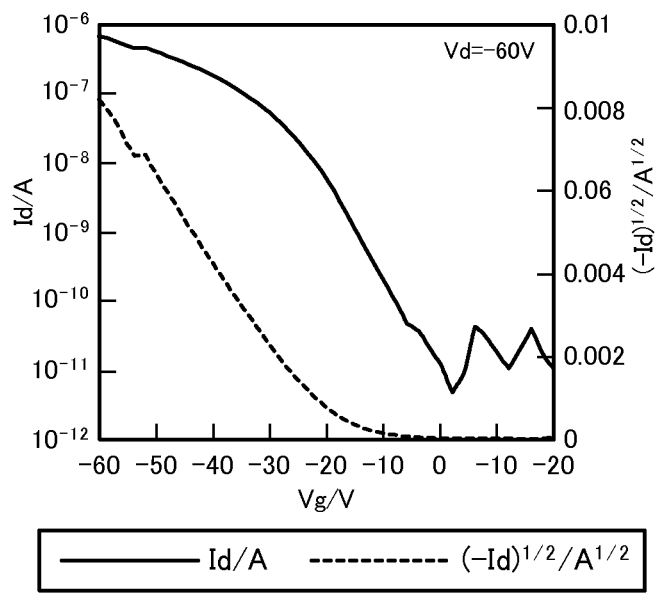
FIG. 3A shows a Vg-Id curve of an FET element produced using a compound B.
Figure 3B:
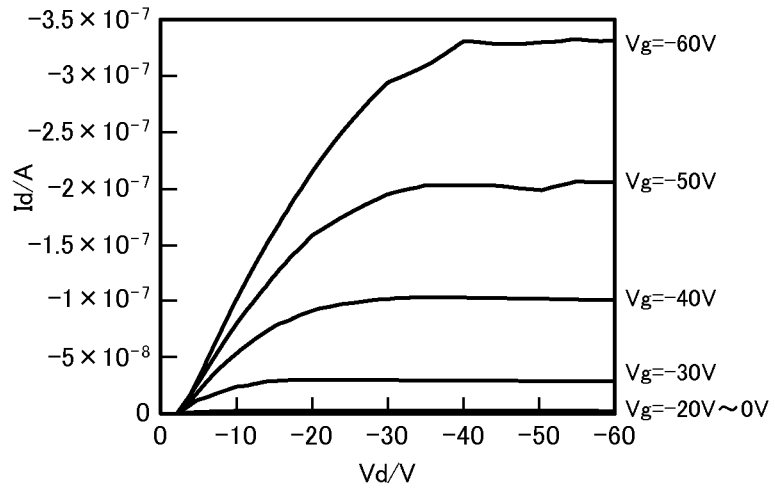
FIG. 3B shows a Vd-Id curve of the FET element.
Figure 4A:
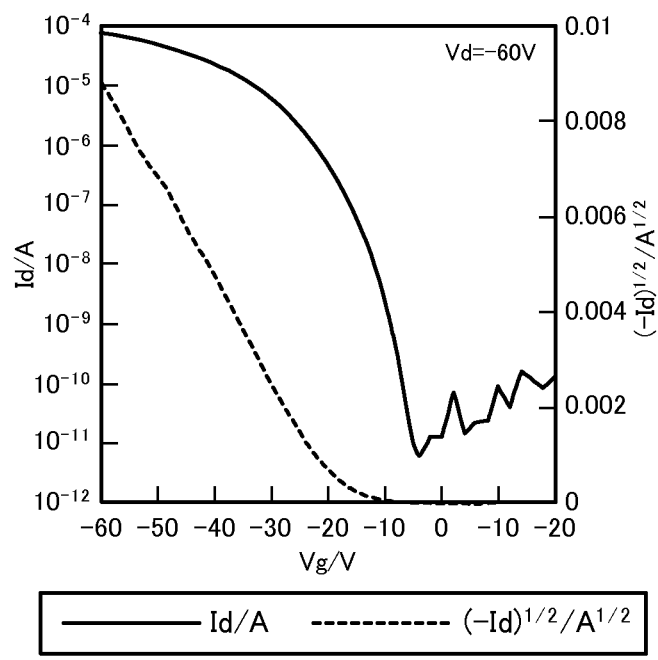
FIG. 4A shows a Vg-Id curve of an FET element produced using a compound C.
Figure 4B:
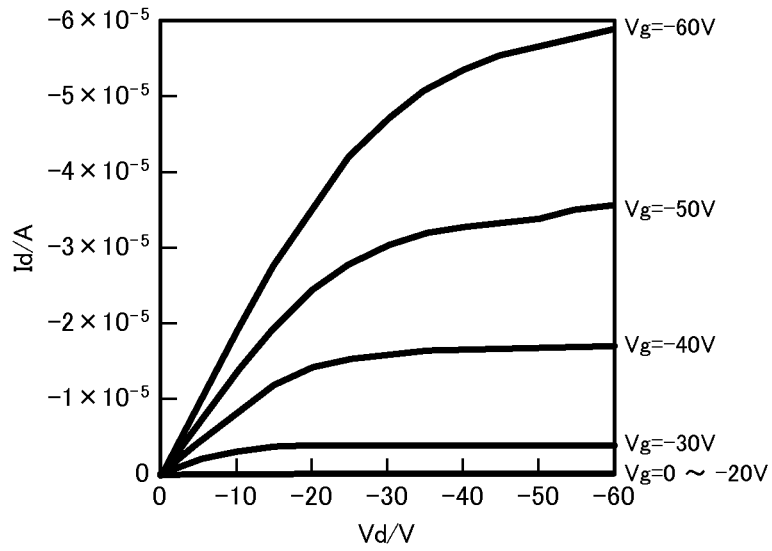
FIG. 4B shows a Vd-Id curve of the FET element.
Figure 5A:
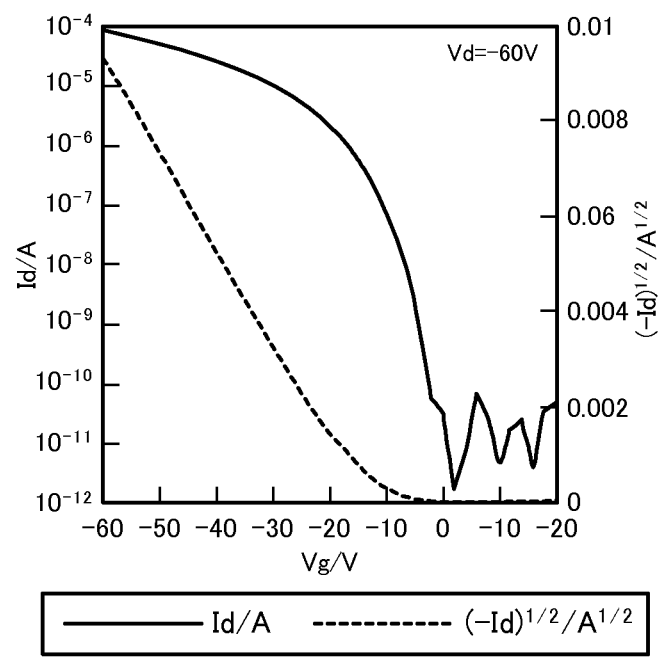
FIG. 5A shows a Vg-Id curve of the FET element produced using a compound D.
Figure 5B:
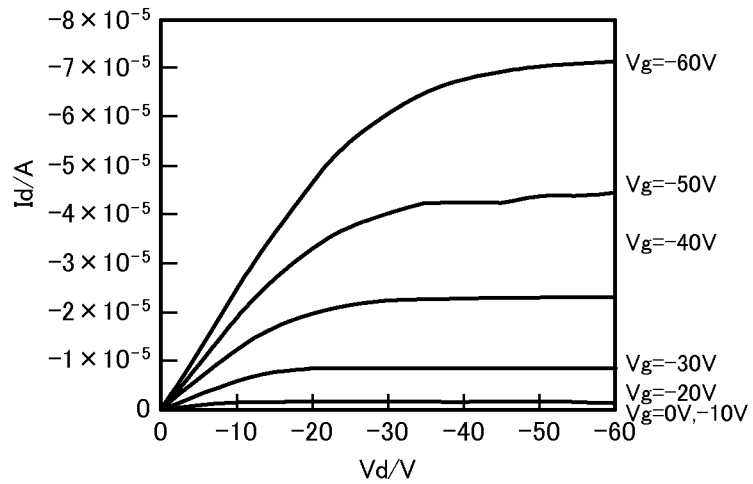
FIG. 5B shows a Vd-Id curve of the FET element.

FIG. 2 is a diagram showing the FET characteristic of the FET device produced using the compound A. FIG. 3 is a diagram showing the FET characteristic of the FET device produced using the compound B. FIG. 4 is a diagram showing the FET characteristic of the FET device produced using the compound C. FIG. 5 is a diagram showing the FET characteristic of the FET device produced using the compound D.

FIGS. 2A, 3A, 4A, and 5A are $V_g$-Id curves of respective FET devices. Moreover, FIGS. 2B, 3B, 4B, and 5B are $V_d$-Id curves of respective FET devices.

The $V_g$-Id curve indicates a relationship between the gate voltage ($V_g$) and the current (Id) when the source-drain voltage (Vd) was fixed so that the current (Id) becomes the value of a saturated current in an output characteristic. That is, the $V_g$-Id curve indicates a transfer characteristic (transmission characteristic) of the corresponding FET device. In the $V_g$-Id curve, the sharper the rising from an off state to an on state is, the better the switching characteristic is, and the transistor characteristic is good. Moreover, the lower an off current is, and the higher an on current is, the larger the on/off ratio becomes, which indicates that the transistor is a good transistor.

Conversely, the $V_d$-Id curve indicates the relationship between the source-drain voltage ($V_d$) and the current (Id) when the gate voltage ($V_g$) is changed step by step. That is, the $V_d$-Id curve indicates the output characteristic (outputting characteristic) of the corresponding FET device. Regarding the FET device, when it is indicated that the current (Id) is saturated (a saturated current) in a range where the source-drain voltage ($V_d$) is high and the current (Id) linearly rises in a range where the source-drain voltage ($V_d$) is low at any gate voltage ($V_g$), such an FET device has a good output characteristic, and has a high-performance.

In all of FIGS. 2A, 3A, 4A, and 5A, the current (Id) sharply rises upon application of the gate voltage ($V_g$). This indicates that the FET device of the present invention has a good switching characteristic. Moreover, in all of FIGS. 2B, 3B, 4B, and 5B, the $V_d$-Id curve substantially linearly rises in a range where the source-drain voltage ($V_d$) is low, and the drain current becomes constant in a range where the source-drain voltage ($V_d$) is high, and a saturated current is observed. This indicates that the FET device of the present invention is a high-performance FET device having a good output characteristic.

Next, the field mobility of the FET device was obtained through the above-explained scheme. In each of the $V_g$-Id curves, a condition when $V_g$ was small from 0 to −10 V was taken as an off state, and a condition when $V_g$ was −60 V was taken as an on state, and the ratio of the value of Id in each of the off state and the on state was obtained as an on/off ratio. The results were as follows. In the case of the FET device using the compound A, the field mobility was 0.7 cm$^2$/Vs, and the on/off ratio was $10^6$. In the case of the FET device using the compound C, the field mobility was 0.2 cm$^2$/Vs, and the on/off ratio was $10^7$. Moreover, in the case of the FET device using the compound D, the field mobility was 0.2 cm$^2$/Vs, and the on/off ratio was $10^7$. Thus, the FET devices using the compounds A, C, and D, respectively, have a good measurement result.

Moreover, the FET device produced through the coating technique (spin coating) using the compound B had the field mobility of $10^{-3}$ cm$^2$/Vs stage, and the on/off ratio of $10^5$ which were slightly poor in comparison with the FET devices using the compounds A, C, and D. However, this FET device also had an FET characteristic, so that it becomes clear that the production method of an FET device according to the present invention can employ a coating technique.

As explained above, the FET devices using the compounds A, B, C, and D synthesized in the above examples can be used as p-type transistors.

This application is based on Japanese Patent Application No. 2008-298830 filed on Nov. 21, 2008 and Japanese Patent Application No. 2009-080527 filed on Mar. 27, 2009. The whole specifications, claims, and drawings of Japanese Patent Application No. 2008-298830 and Japanese Patent Application No. 2009-080527 are herein incorporated in this specification by reference.

INDUSTRIAL APPLICABILITY

The compounds of the present invention have a conjugate system in molecules due to an interaction between π orbitals, and show a strong molecular interaction through a sulfur atom or a selenium atom contained in a thiophene ring or a selenophene ring in each molecule. This allows the compounds of the present invention to move carriers efficiently. Because the compounds have a good field mobility, such compounds can be used as organic semiconductor materials, and organic semiconductor device can be produced using such compounds.

The invention claimed is:

1. A method of producing a compound represented by a following general formula (1), (2), (3) or (4), the method comprising:

a step of causing dihalogenodihydroxynaphthalene to react with an anhydrous trifluoromethanesulfonic acid in order to obtain dihalogeno-bis(trifluoromethanesulfonyl)naphthalene;

a step of causing the dihalogeno-bis(trifluoromethanesulfonyl)naphthalene to react with a terminal acetylene compound in order to obtain a dihalogeno-diethynylnaphthalene derivative; and a step of causing the dihalogeno-diethynylnaphthalene derivative to react with sulfide salt or selenide salt,

[Chemical Formula 1]

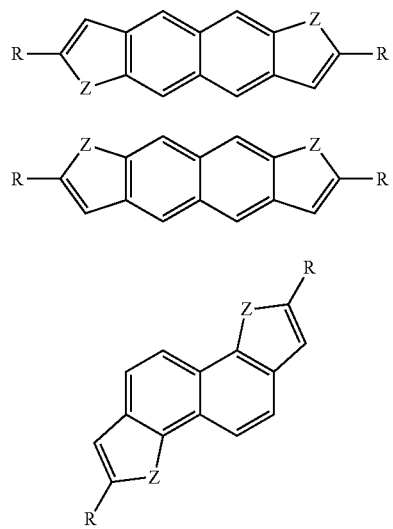

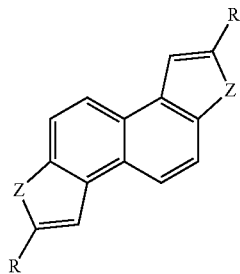

(where Z represents a sulfur atom or a selenium atom, and R represents a hydrogen atom, an alkyl group or a phenyl group in the above general formulae).

2. The method of producing a compound according to claim 1 further comprising a step of causing dihydroxynaphthalene to react with a halogenation agent in order to obtain the dihalogenodihydroxynaphthalene.

3. The method of producing a compound according to claim 2, wherein
the dihydroxynaphthalene is 2,6-dihydroxynaphthalene, and
the compound obtained is a compound represented by the general formula (1) or (3).

4. The method of producing a compound according to claim 2, wherein
the dihydroxynaphthalene is 2,7-dihydroxynaphthalene, and
the compound obtained is a compound represented by the general formula (2).

5. The method of producing a compound according to claim 2, wherein
the dihydroxynaphthalene is 1,5-dihydroxynaphthalene, and
the compound obtained is a compound represented by the general formula (4).

6. The method of producing a compound according to claim 2, wherein the halogenation agent is a bromination agent or a chlorination agent.

7. The method of producing a compound according to claim 6, wherein
the halogenation agent is a bromination agent,
the compound production method further comprises a step of adding a catalyst that promotes bromination of the dihydroxynaphthalene, and
the step of adding the bromination agent is carried out equal to or greater than twice.

8. The method of producing a compound according to claim 1, wherein the terminal acetylene compound is any one of the followings: trimethylsilylacetylene; phenylacetylene; and 1-decyne.

9. The method of producing a compound according to claim 1, wherein the reaction of the dihalogeno-bis(trifluoromethanesulfonyl)naphthalene with the terminal acetylene compound is carried out in a polar solvent that can dissolve the dihalogeno-bis(trifluoromethanesulfonyl)naphthalene.

10. The method of producing a compound according to claim 9, wherein the polar solvent is an aprotic polar solvent.

11. The method of producing a compound according to claim 10, wherein the aprotic polar solvent is dimethylformamide.

* * * * *